(12) United States Patent
Ehsan et al.

(10) Patent No.: US 11,437,606 B2
(45) Date of Patent: Sep. 6, 2022

(54) FABRICATION OF NANOSTRUCTURED PALLADIUM THIN FILM FOR ELECTROCHEMICAL DETECTION OF HYDRAZINE

(71) Applicant: KING FAHD UNIVERSITY OF PETROLEUM AND MINERALS, Dhahran (SA)

(72) Inventors: Muhammad Ali Ehsan, Dhahran (SA); Manzar Sohail, Dhahran (SA); Abbas Saeed Hakeem, Dhahran (SA)

(73) Assignee: KING FAHD UNIVERSITY OF PETROLEUM AND MINERALS, Dhahran (SA)

( * ) Notice: Subject to any disclaimer, the term of this patent is extended or adjusted under 35 U.S.C. 154(b) by 864 days.

(21) Appl. No.: 16/285,653

(22) Filed: Feb. 26, 2019

(65) Prior Publication Data
US 2020/0274135 A1 Aug. 27, 2020

(51) Int. Cl.
| | |
|---|---|
| *H01M 4/04* | (2006.01) |
| *H01M 4/60* | (2006.01) |
| *H01M 4/36* | (2006.01) |
| *G01N 27/26* | (2006.01) |
| *G01N 33/00* | (2006.01) |
| *G01N 27/30* | (2006.01) |
| *H01M 4/02* | (2006.01) |
| *C23C 16/448* | (2006.01) |

(52) U.S. Cl.
CPC .......... *H01M 4/0404* (2013.01); *G01N 27/26* (2013.01); *G01N 27/30* (2013.01); *G01N 33/00* (2013.01); *H01M 4/364* (2013.01); *H01M 4/60* (2013.01); *C23C 16/4486* (2013.01); *H01M 2004/021* (2013.01); *Y02E 60/10* (2013.01)

(58) Field of Classification Search
CPC ......... C23C 16/4486; B22F 9/24; H01M 4/92
USPC .............................. 427/475; 75/355
See application file for complete search history.

(56) References Cited

U.S. PATENT DOCUMENTS

| | | | |
|---|---|---|---|
| 4,992,244 A | 2/1991 | Grate | |
| 2016/0096770 A1 | 4/2016 | Miki Yoshida et al. | |

FOREIGN PATENT DOCUMENTS

| | | |
|---|---|---|
| CA | 852327 A | 9/1970 |
| CN | 104101634 A | 10/2014 |
| JP | 60-263851 A | 12/1985 |

OTHER PUBLICATIONS

Muhammad Ali Ehsan et al, Electrocatalystsis (2019)10:2014-221. (Year: 2019).*

(Continued)

*Primary Examiner* — Tabassom Tadayyon Eslami
(74) *Attorney, Agent, or Firm* — Oblon, McClelland, Maier & Neustadt, L.L.P.

(57) ABSTRACT

A method of making a nanostructured palladium thin film electrode is described. The method involves contacting a substrate with an aerosol comprising a solvent and a Pd(II) compound. The substrate is heated, and no hydrogen gas or an additional reducing agent is required to reduce the Pd(II) to form the deposited thin film. The nanostructured palladium thin film electrode is capable of detecting compounds such as hydrazine in an aqueous sample with a 10 nM limit of detection.

19 Claims, 25 Drawing Sheets

(56) References Cited

OTHER PUBLICATIONS

Liang Xu, et al., "Highly dispersed palladium nanoparticles generated in situ on layered double hydroxide nanowalls for ultrasensitive electrochemical detection of hydrazine", Analytical Methods, vol. 9, Issue 47, Nov. 2017, 2 pages (Abstract only).

Xuan-Hung Pham, et al., "Hydrazine detection by shape-controlled palladium nanostructures on carbon nanotube thin films", Biochip Journal, vol. 7, No. 2, Jun. 2013, pp. 156-163.

Muhammad Ali Ehsan, et al., "Vysotskite structured photoactive palladium sulphide thin films from dithiocarbamate derivatives", New Journal of Chemistry, vol. 38, Issue 9, 2014, pp. 4083-4091.

Atiweena Krittayavathananon, et al., "Palladium Nanoparticles Decorated on Reduced Graphene Oxide Rotating Disk Electrodes toward Ultrasensitive Hydrazine Detection: Effects of Particle Size and Hydrodynamic Diffusion", Analytical Chemistry, vol. 86, 2014, pp. 12272-12278.

Vijay Bhaskaran, et al., "Palladium Thin Films Grown by CVD from (1.1,1,5,5.5-Hexafluoro-2,4-pentanedionato) Palladium(II)", Chemical Vapor Deposition, vol. 3, No. 2, 1997, pp. 85-90.

Yeng-Lien Tung, et al., "Synthesis and Characterization of Allyl(β-ketoiminato)palladium(II) Complexes: New Precursors for Chemical Vapor Deposition of Palladium Thin Films", Organometallics, vol. 18, No. 5, 1999, pp. 864-869.

\* cited by examiner

FABRICATION OF NANOSTRUCTURED PALLADIUM THIN FILM FOR ELECTROCHEMICAL DETECTION OF HYDRAZINE

STATEMENT OF ACKNOWLEDGEMENT

The support of this research and facility utilization is acknowledged from Center of Research Excellence in Nanotechnology (CENT) at King Fahd University of Petroleum and Minerals (KFUPM).

BACKGROUND OF THE INVENTION

Technical Field

The present invention relates to a method of making a palladium thin film electrode that is capable of detecting materials such as hydrazine.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Nobel metal nanomaterials such as Ag, Au, Pd. and Pt are attractive candidates for many applications including wearable/micro-electronics, catalysts, and sensors. See G.-W. Huang, H.-M. Xiao, S.-Y. Fu, Scientific reports 2015, 5, 13971; N. Ly, D. E. Xu, W. H. Song, M. Mayer, Microelectronics Reliability 2015, 55, 201-206; S. E. Kleijn, S. C. Lai, M. T. Koper, P. R. Unwin, Angewandte Chemie International Edition 2014, 53, 3558-3586; A. Chen, C. Ostrom, Chemical reviews 2015, 115, 11999-12044; and S. Guo, E. Wang, Nano Today 2011, 6, 240-264; bP. K. Jain, X. Huang, I. H. El-Sayed, M. A. El-Sayed, Accounts of chemical research 2008, 41, 1578-1586, each incorporated herein by reference in their entirety. Such metallic nanomaterials present remarkable conductivities, enhanced specific surface areas, and a higher number of active sites which constitute a new class of smart materials with better analytical performance. Among these metallic resources, palladium based nanomaterials have been widely used as potential electrochemical sensors for the detection of gases such as hydrogen, and methane, and physiological molecules such as uric acid, glucose, dopamine, ascorbic acid, hydrazine, and formaldehyde. See D. H. Shin, J. S. Lee, J. Jun, J. H. An, S. G. Kim, K. H. Cho, J. Jang, Scientific reports 2015, 5, 12294; Z. Li, J. Zhang, Y. Zhou, S. Shuang, C. Dong, M. M. Choi, Electrochimica Acta 2012, 76, 288-291; A. A. Rafati, A. Afraz, A. Hajian, P. Assari, Microchimica Acta 2014, 181, 1999-2008; X. Jia, G. Hu, F. Nitze, H. R. Barzegar, T. Sharifi, C.-W. Tai, T. Wågberg, ACS applied materials & interfaces 2013, 5, 12017-12022; S. Palanisamy, S. Ku, S.-M. Chen, Microchimica Acta 2013, 180, 1037-1042; S. Palanisamy et al.; S. Sakthinathan, S. Kubendhiran, S. M. Chen, P. Sireesha, C. Karuppiah, C. Su, Electroanalysis 2017, 29, 587-594; and I. Pötzelberger, C. C. Mardare, W. Burgstaller, A. W. Hassel, Applied Catalysis A: General 2016, 525, 110-118, each incorporated herein by reference in their entirety. Despite the excellent catalytic activities, the customary use of Pd films in electrochemical sensors is restricted by the lack of an efficient deposition method to produce homogenous nanostructured thin films in a single step.

Compared to various other synthetic routes, chemical vapor deposition (CVD) method has been extensively investigated for the deposition of Pd thin films. See A. Chen, C. Ostrom, Chemical reviews 2015, 115, 11999-12044; and R. Westerström, M. Messing, S. Blomberg, A. Hellman, H. Gronbeck, J. Gustafson, N. Martin, O. Balmes, R. Van Rijn, J. N. Andersen, Physical Review B 2011, 83, 115440; bA. Das, D. H. Ko, C.-H. Chen, L.-B. Chang, C.-S. Lai, F.-C. Chu, L. Chow, R.-M. Lin, Sensors and Actuators B: Chemical 2014, 205, 199-205; Y. Qin, A. U. Alam, M. M. Howlader, N. X. Hu, M. J. Deen, Advanced Functional Materials 2016, 26, 4923-4933; each incorporated herein by reference in their entirety. However, the Pd film precursors examined for CVD were either thermally unstable or exhibited circumscribed volatility, which severely affected the film deposition process including slower growth rates and incorporation of impurities from precursor compounds. See V. Bhaskaran, M. J. Hampden-Smith, T. T. Kodas, Chemical Vapor Deposition 1997, 3, 281-286; N. L. Jeon, W. Lin, M. K. Erhardt, G. S. Girolami, R. G. Nuzzo, Langmuir 1997, 13, 3833-3838; Y.-L. Tung, W.-C. Tseng, C.-Y. Lee, P.-F. Hsu, Y. Chi, S.-M. Peng, G.-H. Lee, Organometallics 1999, 18, 864-869; J. E. Gozum, D. M. Pollina, J. A. Jensen, G. S. Girolami, Journal of the American Chemical Society 1988, 110, 2688-2689; Z. Yuan, D. Jiang, S. Naftel, T.-K. Sham, R. J. Puddephatt, Chemistry of materials 1994, 6, 2151-2158, incorporated herein by reference in its entirety. As a result, the films deposited were undesirable for electrochemical sensing. In some reports, a hydrogen gas supply was also required to reduce Pd (II) ions to metallic Pd, which makes the CVD process more inconvenient. Surprisingly, to resolve the precursor issues, alternative deposition options such as aerosol assisted CVD (AACVD) are relatively less explored for the fabrication of nano-sized Pd films. See C. Xu, M. J. Hampden-Smith, T. T. Kodas, Advanced Materials 1994, 6, 746-748, incorporated herein by reference in its entirety. In AACVD, the precursor compound is merely required to be soluble instead of being volatile and/or thermally stable. See C. E. Knapp, C. J. Carmalt, Chemical Society Reviews 2016, 45, 1036-1064; P. Marchand, C. J. Carmalt, Coordination Chemistry Reviews 2013, 257, 3202-3221, incorporated herein by reference in its entirety. Also, AACVD can use commercially available precursors; therefore, multistep synthesis steps involved in preparing specific precursor compounds are not necessary. See M. A. Ehsan, M. A. Aziz, A. Rehman, A. S. Hakeem, M. A. A. Qasem, S. H. A. Ahmad, Journal of The Electrochemical Society 2018, 165, B302-B309; R. Naeem, R. Yahya, A. Pandikumar, H. N. Ming, M. Mazhar, Journal of Materials Science: Materials in Electronics 2017, 28, 868-877, incorporated herein by reference in its entirety. However, single step AACVD to form continuous electroactive Pd-films has not been demonstrated.

Herein, a deposition protocol is presented for Pd thin films utilizing commercially available palladium acetylacetonate $Pd(acac)_2$ precursor in the AACVD without supplying hydrogen gas or any other reducing agent during the growth process. Previously, this precursor had encountered volatility problems when used in low-pressure CVD, but here the precursor delivery and film growth procedure differs from the reported procedure. See V. Bhaskaran, M. J. Hampden-Smith, T. T. Kodas, Chemical Vapor Deposition 1997, 3, 281-286, incorporated herein by reference in its entirety. Moreover, this precursor is adequately soluble in toluene to make an aerosol and thermally stable enough to endure temperatures of 475° C. to generate ionic/gaseous species. The solubility and thermal stability both make film formation more convenient and controllable. Thus, a single step AACVD approach is established to produce nanostructured Pd-films on FTO substrates.

The electrochemical behavior of the produced films is tested without any surface alteration, for which hydrazine was used as the target analyte. Hydrazine is a colorless, flammable, and toxic chemical. The consumption of hydrazine is routinely observed in various industries, for example as an additive in rocket fuels, photographic chemicals, agro-chemicals, emulsifiers, blowing agents, textile dyes, and corrosion inhibitors in various industries. See L. Cui, C. Ji, Z. Peng, L. Zhong, C. Zhou, L. Yan, S. Qu, S. Zhang, C. Huang, X. Qian, *Analytical chemistry* 2014, 86, 4611-4617, incorporated herein by reference in its entirety. Despite its widespread use, hydrazine is highly mutagenic and carcinogenic, and its acute exposure can severely damage human body parts such as lungs, liver, kidneys, brain, and spinal cord. See S. Dutta, C. Ray, S. Mallick, S. Sarkar, A. Roy, T. Pal, *RSC Advances* 2015, 5, 51690-51700; B. Zhou, J. Yang, X. Jiang, *Materials Letters* 2015, 159, 362-365, incorporated herein by reference in its entirety. The United States Environmental Protection Agency (US EPA) considers hydrazine a human carcinogen placed in group B2. See L. Cui, Z. Peng, C. Ji, J. Huang, D. Huang, J. Ma, S. Zhang, X. Qian, Y. Xu, *Chemical Communications* 2014, 50, 1485-1487, incorporated herein by reference in its entirety. Thus, it is necessary to develop a simple, cost-effective, fast, selective, and sensitive analytical setup for the accurate monitoring of trace hydrazine in the environment.

Compared with other methods that have been used for the detection of hydrazine, electrochemical analysis is of huge interest because of its simplicity, cost-effectiveness, high sensitivity, selectivity, and in-situ determination. See S. Subramanian, S. Narayanasastri, A. R. K. Reddy, *RSC Advances* 2014, 4, 27404-27413; M. Sun, L. Bai, D. Q. Liu, *Journal of pharmaceutical and biomedical analysis* 2009, 49, 529-533; A. Safavi, M. A. Karimi, *Talanta* 2002, 58, 785-792; Y. J. Yang, W. Li, X. Wu, *Electrochimica Acta* 2014, 123, 260-267; C. Karuppiah, S. Palanisamy, S.-M. Chen, S. K. Ramaraj, P. Periakaruppan, *Electrochimica Acta* 2014, 139, 157-164; and G. Wang, C. Zhang, X. He, Z. Li, X. Zhang, L. Wang, B. Fang, *Electrochimica Acta* 2010, 55, 7204-7210; R. Devasenathipathy, V. Mani, S.-M. Chen, *Talanta* 2014, 124, 43-51; X. Chen, W. Liu, L. Tang, J. Wang, H. Pan, M. Du, *Materials Science and Engineering: C* 2014, 34, 304-310, each incorporated herein by reference in its entirety. In order to enhance hydrazine sensing performance, conventional electrodes such as a composite of palladium nanoparticles and reduced graphene oxide, TiOz nanoparticles modified glassy carbon electrode, hollow ZnS decorated with gold nanoparticles, single walled carbon nanohoms/gold nanocomposite, and Zn-MOF over a glassy carbon electrode have been employed. See A. Krittayavathananon, P. Srimuk, S. Luanwuthi, M. Sawangphruk, *Analytical chemistry* 2014, 86, 12272-12278; M. M. Rahman, V. G. Alfonso, F. Fabregat-Santiago, J. Bisquert, A. M. Asiri, A. A. Alshehri, H. A. Albar, *Microchimica Acta* 2017, 184, 2123-2129; F. Feng, Z. Ma, *Sensors and Actuators B: Chemical* 2016, 232, 9-15; S. Zhao, L. Wang, T. Wang, Q. Han, S. Xu, *Applied Surface Science* 2016, 369, 36-42; and M. Sohail, M. Altaf, N. Baig, R. Jamil, M. Sher, A. Fazal, *New Journal of Chemistry* 2018, each incorporated herein by reference in their entirety. However, the exploration of low cost, simple, and rapid fabrication strategies for the synthesis of fast and sensitive response sensing materials in novel morphologies for hydrazine oxidation is still continued. Pd films described herein were explored for a platform which is simple, low-cost, and biologically safe for the detection of hydrazine. The sensing parameters such as sensitivity, selectivity, response time, robustness, and detection limit of the Pd-thin film electrode deposited on the FTO electrode (Pd-thin film/FTO) were determined.

In view of the forgoing, one objective of the present invention is to provide a method for making a palladium thin film electrode, which involves a one-step deposition by AACVD. The method does not require the use of hydrogen gas or a reducing agent, and generates a nanostructured thin film of palladium which may be used for the detection of hydrazine.

BRIEF SUMMARY OF THE INVENTION

According to a first aspect, the present disclosure relates to a method of making a Pd thin film electrode. The method involves depositing a crystalline Pd layer on a substrate by contacting an aerosol with a substrate to form a Pd thin film electrode. The aerosol comprises a carrier gas and a Pd(II) compound dissolved in a solvent, and the substrate has a temperature of no greater than 550° C.

In one embodiment, the temperature is in a range of 400-500° C.

In one embodiment, the aerosol and substrate do not comprise or contact hydrogen gas or a reducing agent during the depositing.

In one embodiment, the Pd thin film electrode comprises a Pd film having an average thickness of 0.5-2.0 μm in contact with the substrate, and Pd agglomerates on the Pd film.

In a further embodiment, the Pd agglomerates have an average diameter of 100-400 nm, and the Pd agglomerates comprise Pd nanoparticles having an average diameter of 10-75 nm.

In one embodiment, before the depositing, the aerosol consists essentially of the carrier gas, the solvent, and the Pd(II) compound.

In one embodiment, the palladium(II) compound and the solvent are present in the aerosol at a weight ratio in a range of 1:1000 to 1:2.

In one embodiment, the substrate is a transparent conducting film selected from the group consisting of ITO (indium tin oxide), FTO (fluorine-doped tin oxide), AZO (aluminum-doped zinc oxide), GZO (gallium-doped zinc oxide), IZO (indium zinc oxide), IZTO (indium zinc tin oxide), IAZO (indium aluminum zinc oxide), IGZO (indium gallium zinc oxide), IGTO (indium gallium tin oxide), and ATO (antimony tin oxide).

In one embodiment, the substrate has a sheet resistance in a range of 1-110 D/sq.

In one embodiment, the Pd(II) compound is at least one selected from the group consisting of palladium(II) acetate, palladium(II) bromide, palladium(II) chloride, palladium(II) fluoride, palladium(II) iodide, palladium(II) nitrate, palladium(II) cyanide, sodium tetrachloropalladate, bis(triphenylphosphine)palladium chloride, palladium(II) acetylacetonate, and palladium(II) hexafluoroacetylacetonate.

In a further embodiment, the Pd(II) compound is palladium acetylacetonate.

In one embodiment, the solvent is at least one selected from the group consisting of pyridine, N,N-dimethylformamide (DMF), N,N-dimethylacetamide, N-methyl pyrrolidone (NMP), hexamethylphosphoramide (HMPA), dimethyl sulfoxide (DMSO), acetonitrile, tetrahydrofuran (THF), 1,4- dioxane, dichloromethane, chloroform, carbon tetrachloride, dichloroethane, acetone, ethyl acetate, pentane, hexane, decalin, THF, dioxane, benzene, toluene, xylene, o-dichlorobenzene, diethyl ether, methyl t-butyl ether, methanol, ethanol, ethylene glycol, isopropanol, propanol, and n-butanol.

In one embodiment, the solvent is toluene.

In one embodiment, the carrier gas is $N_2$, Ar, or compressed air.

In one embodiment, the aerosol is introduced to the substrate for a time period of 10 min-2 h.

In one embodiment, during the introducing of the aerosol, the carrier gas has a flow rate in a range of 0.1 to 10 mL/s.

In one embodiment, the Pd thin film electrode detects hydrazine in an aqueous solution with a limit of detection (LOD) in a range of 1-50 nM.

In one embodiment, the Pd thin film electrode detects hydrazine in an aqueous solution with a limit of quantification (LOQ) in a range of 1-50 nM.

In one embodiment, the Pd thin film electrode detects hydrazine in an aqueous solution with a linear chronoamperometric response over a hydrazine concentration of 0.5-350 μM.

According to a second aspect, the present disclosure relates to a Pd thin film electrode manufactured by the method of claim 1.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
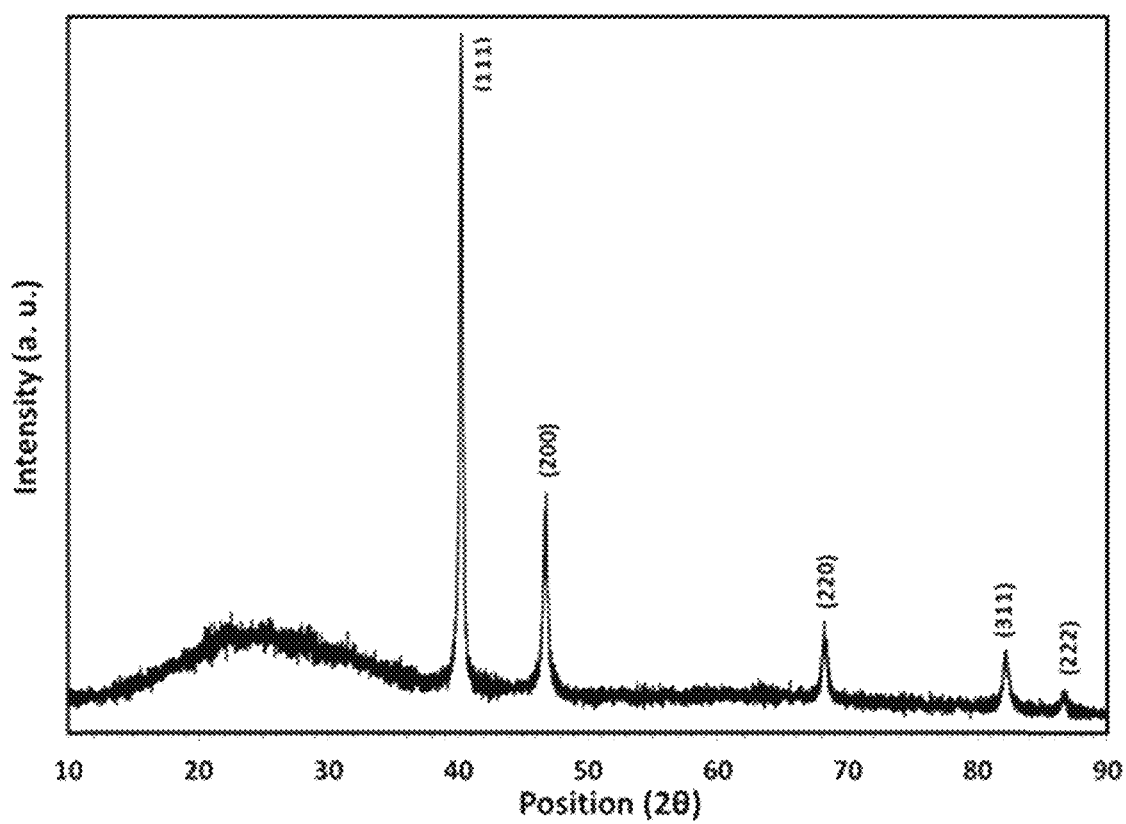
FIG. 1 is an X-ray diffraction (XRD) pattern of palladium film deposited on glass.

Embodiments of the present disclosure will now be described more fully hereinafter with reference to the accompanying drawings, in which some, but not all embodiments of the disclosure are shown.

The present disclosure will be better understood with reference to the following definitions. As used herein, the words "a" and "an" and the like carry the meaning of "one or more." Within the description of this disclosure, where a numerical limit or range is stated, the endpoints are included unless stated otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the words "about," "approximately," or "substantially similar" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), or +/−20% of the stated value (or range of values). Within the description of this disclosure, where a numerical limit or range is stated, the endpoints are included unless stated otherwise. Also, all values and subranges within a numerical limit or range are specifically included as if explicitly written out.

As used herein, "compound" or "complex" is intended to refer to a chemical entity, whether as a solid, liquid, or gas, and whether in a crude mixture or isolated and purified.

As used herein, "composite" refers to a combination of two or more distinct constituent materials into one. The individual components, on an atomic level, remain separate and distinct within the finished structure. The materials may have different physical or chemical properties, that when combined, produce a material with characteristics different from the original components. In some embodiments, a composite may have at least two constituent materials that comprise the same empirical formula but are distinguished by different densities, crystal phases, or a lack of a crystal phase (i.e. an amorphous phase).

The present disclosure is intended to include all hydration states of a given compound or formula, unless otherwise noted or when beating a material. For example, $Ni(NO_3)_2$ includes anhydrous $Ni(NO_3)_2$, $Ni(NO_3)_2 \cdot 6H_2O$, and any other hydrated forms or mixtures. $CuCl_2$ includes both anhydrous $CuCl_2$ and $CuCl_2 \cdot 2H_2O$.

In addition, the present disclosure is intended to include all isotopes of atoms occurring in the present compounds and complexes. Isotopes include those atoms having the same atomic number but different mass numbers. By way of general example, and without limitation, isotopes of hydrogen include deuterium and tritium. Isotopes of carbon include $^{13}C$ and $^{14}C$. Isotopes of nitrogen include $^{14}N$ and $^{15}N$. Isotopes of oxygen include $^{16}O$, $^{17}O$, and $^{18}O$. Isotopes of palladium include $^{102}Pd$, $^{104}Pd$, $^{105}Pd$, $^{106}Pd$, $^{107}Pd$, $^{108}Pd$, and $^{110}Pd$. Isotopically-labeled compounds of the disclosure may generally be prepared by conventional techniques known to those skilled in the art or by processes analogous to those described herein, using an appropriate isotopically-labeled reagent in place of the non-labeled reagent otherwise employed.

As defined here, an aerosol is a suspension of solid or liquid particles in a gas. An aerosol includes both the particles and the suspending gas. Primary aerosols contain particles introduced directly into the gas, while secondary aerosols form through gas-to-particle conversion. There are several measures of aerosol concentration. Environmental science and health fields often use the mass concentration (M), defined as the mass of particulate matter per unit volume with units such as $\mu g/m^3$. Also commonly used is the number concentration (N), the number of particles per unit volume with units such as $number/m^3$ or $number/cm^3$. The size of particles has a major influence on their properties, and the aerosol particle radius or diameter ($d_p$) is a key property used to characterize aerosols. Aerosols vary in their dispersity. A monodisperse aerosol, producible in the laboratory, contains particles of uniform size. Most aerosols, however, as polydisperse colloidal systems, exhibit a range of particle sizes. Liquid droplets are almost always nearly spherical, but scientists use an equivalent diameter to characterize the properties of various shapes of solid particles, some very irregular. The equivalent diameter is the diameter of a spherical particle with the same value of some physical property as the irregular particle. The equivalent volume diameter ($d_e$) is defined as the diameter of a sphere of the same volume as that of the irregular particle. Also commonly used is the aerodynamic diameter. The aerodynamic diameter of an irregular particle is defined as the diameter of the spherical particle with a density of $1000$ $kg/m^3$ and the same settling velocity as the irregular particle.

As defined here, an electrode is an electrically conductive material comprising a metal and is used to establish electrical contact with a nonmetallic part of a circuit. An "electrically-conductive material" as defined here is a substance with an electrical resistivity of at most $10^{-6}$ $\Omega \cdot m$, preferably at most $10^{-7}$ $\Omega \cdot m$, more preferably at most $10^{-8}$ $\Omega \cdot m$ at a temperature of 20-25° C. The electrically-conductive material comprise platinum-iridium alloy, iridium, titanium, titanium alloy, stainless steel, gold, cobalt alloy, copper, aluminum, tin, iron, and/or some other metal.

According to a first aspect, the present disclosure relates to a method of making a Pd thin film electrode. The method involves depositing a crystalline Pd layer on a substrate by contacting an aerosol with a substrate to form a Pd thin film electrode. The aerosol comprises a carrier gas and a Pd(II) compound dissolved in a solvent.

In one embodiment, the Pd thin film electrode comprises a Pd film having an average thickness of 0.5-2.0 μm, preferably 0.7-1.5 μm, more preferably 0.8-1.2 μm, even more preferably 0.9-1.1 μm, or about 1 μm in contact with the substrate. However, in alternative embodiments, the Pd film may have an average thickness of less than 0.5 μm or greater than 2.0 μm.

The Pd thin film electrode further comprises Pd agglomerates on the Pd film, however, in alternative embodiments, the Pd thin film electrode comprises a Pd film without Pd agglomerates. In one embodiment, the Pd agglomerates have an average diameter of 100-400 nm, preferably 150-350 nm, more preferably 200-300 nm, even more preferably 220-280 nm, and the Pd agglomerates comprise Pd nanoparticles. As used herein, the term "Pd agglomerates" refers to a clustered particulate composition comprising Pd nanoparticles, the Pd nanoparticles being aggregated together in such a way so as to form clusters thereof, at least 50 volume percent of the clusters having a mean diameter that is at least 2 times the mean diameter of the Pd nanoparticles, and preferably at least 90 volume percent of the clusters having a mean diameter that is at least 5 times the mean diameter of the Pd nanoparticles. The Pd nanoparticles may have an average (mean) diameter of 10-75 nm, preferably 20-70 nm, more preferably 25-60 nm, even more preferably 30-55 nm. A Pd thin film electrode comprising Pd agglomerates on a Pd film may be considered nanostructured. In some embodiments, the Pd film and Pd agglomerates have an average combined thickness of 0.5-2.0 μm, preferably 0.7-1.5 μm, more preferably 0.8-1.2 μm, even more preferably 0.9-1.1 μm, or about 1 μm. The Pd thin film electrode may have a surface area per mass Pd of 80-350 $m^2/g$, preferably 100-250 $m^2/g$, even more preferably 120-220 $m^2/g$.

In one embodiment, the Pd agglomerates and/or Pd nanoparticles are monodisperse, having a coefficient of variation or relative standard deviation, expressed as a percentage and defined as the ratio of the particle diameter standard deviation ($\sigma$) to the particle diameter mean ($\mu$), multiplied by 100%, of less than 25%, preferably less than 10%, preferably less than 8%, preferably less than 6%, preferably less than 5%. In a preferred embodiment, the Pd agglomerates and/or Pd nanoparticles are monodisperse having a particle diameter distribution ranging from 80% of the average particle diameter to 120% of the average particle diameter, preferably 85-115%, preferably 90-110% of the average particle diameter. In another embodiment, the Pd agglomerates and/or Pd nanoparticles are not monodisperse.

In one embodiment, the Pd nanoparticles may be substantially spherical, meaning that the distance from the particle centroid (center of mass) to anywhere on the nanoparticle outer surface varies by less than 30%, preferably by less than 20%, more preferably by less than 10% of the average distance. In one embodiment, the Pd nanoparticles may not be substantially spherical and instead shaped like cylinders, boxes, spikes, flakes, plates, ellipsoids, toroids, stars, ribbons, discs, rods, granules, prisms, cones, flakes, platelets, sheets, or some other shape.

In one embodiment, the Pd film and/or Pd agglomerates consist essentially of Pd metal. For instance, the Pd film and/or Pd agglomerates may comprise at least 99 wt %, preferably at least 99.5 wt %, more preferably at least 99.9 wt %, even more preferably at least 99.99 wt % Pd metal relative to a total weight of the Pd film and/or Pd agglomerates.

In one embodiment, the Pd film and/or Pd agglomerates comprise crystalline Pd, for instance, Pd crystallized in a cubic crystal structure. In one embodiment, at least 80 wt %, preferably at least 85 wt %, more preferably at least 95 wt % of the Pd is crystalline Pd. Where the Pd film and/or Pd agglomerates comprise less than 100 wt % crystalline Pd, the remaining Pd may be in an amorphous (non-crystalline) phase. In one embodiment, the Pd film and/or Pd agglomerates are essentially free of palladium black, meaning that the Pd film and/or Pd agglomerates comprise less than 0.1 wt %, preferably less than 0.01 wt % palladium black relative to a total weight of the Pd film and/or Pd agglomerates.

In one embodiment, the thickness of palladium thin film electrode may vary from location to location on the electrode by 1%-15%, by 3%-10%, or by 5%-8% relative to the average thickness.

According to a second aspect, the present disclosure relates to a Pd thin film electrode manufactured by the method described herein, having one or more properties as described above.

As mentioned above, the method involves depositing a crystalline Pd layer on a substrate by contacting an aerosol with a substrate to form a Pd thin film electrode. In one embodiment, the substrate has a temperature of no greater than 575° C., preferably no greater than 550° C., more preferably no greater than 525° C., even more preferably no greater than 500° C. In some embodiments, the substrate will not have a temperature or be heated above 490° C., 480° C., or 475° C. In one embodiment, the temperature of the substrate during the introducing or depositing is in a range of 400-500° C., preferably 420-490° C., more preferably 440-485° C., even more preferably 470-480° C., or about 475° C.

In one embodiment, the substrate is a transparent conducting film selected from the group consisting of ITO (indium tin oxide), FTO (fluorine-doped tin oxide), AZO (aluminum-doped zinc oxide), GZO (gallium-doped zinc oxide), IZO (indium zinc oxide), IZTO (indium zinc tin oxide), IAZO (indium aluminum zinc oxide), IGZO (indium gallium zinc oxide), IGTO (indium gallium tin oxide), and ATO (antimony tin oxide). The transparent conducting film may further be attached to an additional support, such as a glass slide. However, in other embodiments, the substrate may be glass, quartz, ceramic, a metal, a composite material, or a polymeric material having temperature resistance at least up to the temperature of the substrate heating. In one embodiment, the substrate has a sheet resistance in a range of 1-110 Ω/sq, preferably 2-80 Ω/sq, more preferably 4-10 Ω/sq, even more preferably 6-8 Ω/sq. In one embodiment, the substrate (and preferably, any substrate support) is essentially free of Ni, meaning that the substrate comprises less than 0.1 wt %, preferably less than 0.01 wt % Ni relative to a total weight of the substrate. The substrate may have an average thickness of 500 nm-5 mm, preferably 1 μm-500 μm, more preferably 10 μm-50 μm. However, in some embodiments, the substrate may have an average thickness of less than 500 nm or greater than 5 mm.

The aerosol comprises a carrier gas and a Pd(II) compound dissolved in a solvent. In one embodiment, the palladium(II) compound and the solvent are present at a weight ratio in a range of 1:1000-1:2, preferably 1:800-1:10, more preferably 1:500-1:50, even more preferably 1:150-1:120, or about 1:100. However, in some embodiments, the weight ratio may be lower than 1:1000 or greater than 1:2.

In one embodiment, the aerosol may have a mass concentration M, of 10 μg/m$^3$-1,000 mg/m$^3$, preferably 50 μg/m$^3$-1,000 μg/m$^3$. In one embodiment, the aerosol may have a number concentration N, $10^3$-$10^6$, preferably $10^4$-$10^5$ cm$^{-3}$. In other embodiments, the aerosol may have a number concentration of less than $10^3$ or greater than $10^6$. The aerosol particles or droplets may have an equivalent volume diameter ($d_v$) in a range of 20 nm-100 μm, preferably 0.5-70 μm, more preferably 1-50 μm, though in some embodiments, aerosol particles or droplets may have an average diameter of smaller than 0.2 μm or larger than 100 μm.

In one embodiment, the aerosol and substrate do not comprise or contact hydrogen gas or a reducing agent during the contacting and/or depositing. In a related embodiment, the aerosol and substrate do not comprise or contact hydrogen gas or a reducing agent immediately prior to the contacting and/or depositing. In one embodiment, the reaction chamber where the depositing takes place is essentially free of hydrogen gas and a reducing agent immediately prior to the contacting. In one embodiment, an intermediate reducing agent is created during the contacting.

In a related embodiment, before the contacting and/or depositing, the aerosol consists essentially of the carrier gas, the solvent, and the Pd(II) compound, meaning that at least 99.9 wt %, preferably at least 99.99 wt %, or 100 wt % of the aerosol is carrier gas, solvent, or Pd(II) compound, relative to a total weight of the aerosol.

In one embodiment, the Pd(II) compound comprises palladium(II) acetate, palladium(II) bromide, palladium(II) chloride, palladium(II) fluoride, palladium(II) iodide, palladium(II) cyanide, palladium (II) nitrate, sodium tetrachloropalladate, bis(triphenylphosphine)palladium chloride, palladium(II) acetylacetonate, and/or palladium(II) hexafluoroacetylacetonate. Preferably the Pd(II) compound comprises palladium(II) acetate, palladium(II) acetylacetonate, and/or palladium(II) hexafluoroacetylacetonate. In a further embodiment, the Pd(II) compound is palladium acetylacetonate. In other embodiments, an alternative source of Pd, including Pd in different oxidation states (0, +1, +3, +4) may be used to form the palladium thin film electrode. In one embodiment, the Pd(II) compound comprises palladium(II) xanthate or allyl palladium(II) xanthate.

In one embodiment, the solvent comprises pyridine, N,N-dimethylformamide (DMF), N,N-dimethylacetamide, N-methyl pyrrolidone (NMP), hexamethylphosphoramide (HMPA), dimethyl sulfoxide (DMSO), acetonitrile, tetrahydrofuran (THF), 1,4-dioxane, dichloromethane, chloroform, carbon tetrachloride, dichloroethane, acetone, ethyl acetate, pentane, hexane, decalin, THF, dioxane, benzene, toluene, xylene, o-dichlorobenzene, diethyl ether, methyl t-butyl ether, methanol, ethanol, ethylene glycol, isopropanol, propanol, and/or n-butanol. In one embodiment, the solvent is toluene, and in another embodiment, the solvent consists essentially of toluene. Preferably the solvent and Pd(II) compound are able to form an appropriately soluble solution that can be dispersed in the carrier gas as aerosol particles. For instance, the Pd(II) compound may first be dissolved in a volume of solvent, and then pumped through a jet nozzle in order to create an aerosol mist. In other embodiments, the mist may be generated by a piezoelectric ultrasonic generator. Other nebulizers and nebulizer arrangements may also be used, such as concentric nebulizers, cross-flow nebulizers, entrained nebulizers, V-groove nebulizers, parallel path nebulizers, enhanced parallel path nebulizers, flow blurring nebulizers, and piezoelectric vibrating mesh nebulizers.

In one embodiment, the solvent may comprise water. The water used as a solvent or for other purposes may be tap water, distilled water, bidistilled water, deionized water, deionized distilled water, reverse osmosis water, and/or some other water. In one embodiment the water is bidistilled or treated with reverse osmosis to eliminate trace metals. Preferably the water is bidistilled, deionized, deionized distilled, or reverse osmosis water, and at 25° C. has a conductivity of less than 10 $\mu S \cdot cm^{-1}$, preferably less than 1 $\mu S \cdot cm^{-1}$; a resistivity of greater than 0.1 MΩ·cm, preferably greater than 1 MΩ·cm, more preferably greater than 10 MΩ·cm; a total solid concentration of less than 5 mg/kg, preferably less than 1 mg/kg; and a total organic carbon concentration of less than 1000 μg/L, preferably less than 200 μg/L, more preferably less than 50 μg/L.

In one embodiment, the carrier gas is $N_2$, He, compressed air, and/or Ar. Preferably the carrier gas is $N_2$.

In one embodiment, the aerosol is contacted to the substrate for a time period of 10 min-2 h, preferably 15 min-1.5 h, more preferably 20 min-45 min, even more preferably about 30 min. However, in some embodiments, the aerosol may be introduced for a time period of less than 10 min or greater than 2 h. As used herein, "introducing" and/or "contacting" the aerosol with the substrate means that the substrate is exposed to the aerosol, so that a portion of the suspended particles of the aerosol directly contact the substrate. The method of producing the palladium thin film electrode may be considered a one-step method, as the reduction of the Pd(II) compound and the deposition of the Pd takes place immediately following and/or during the contacting of the aerosol with the substrate.

The contacting and/or introducing may take place within a closed chamber or reactor, and the aerosol may be generated by dispersing a solution of the Pd(II) compound and solvent. In one embodiment, this dispersing may be increased by fans, jets, or pumps. However, in another embodiment, an aerosol may be formed in a closed chamber with a substrate where the aerosol particles are allowed to diffuse towards or settle on the substrate. The closed chamber or reactor may have an interior volume of 0.2-100 L, preferably 0.3-25 L, more preferably 0.5-10 L. In one embodiment, the closed chamber or reactor may comprise a cylindrical glass vessel, such as a glass tube.

Being in a closed chamber, the interior pressure of the chamber (and thus the pressure of the aerosol) may be controlled. The pressure may be practically unlimited, but need not be an underpressure or an overpressure. The pressure may range from 200 to 1000, 350 to 900, 500 to 850, 600 to 800, 700 to 790, or 750 to 780 mm Hg, or the pressure may be ambient pressure.

In one embodiment, this introducing/contacting and depositing step is equivalent to aerosol assisted chemical vapor deposition (AACVD).

In one embodiment, during the contacting of the aerosol, the carrier gas has a flow rate in a range of 0.1 to 10 mL/s, preferably 0.5 to 7.5 mL/s, more preferably 1.5 to 5.0, even more preferably 2.0-4.0 mL/s, or about 2.5 mL/s (equivalently 150 $cm^3$/min). Preferably the aerosol has the same flow rate as the carrier gas.

During the contacting of the aerosol, the Pd film and/or Pd agglomerates may form at a rate of 0.1 to 20, 0.2 to 20, 0.4 to 20, 0.5 to 20, 0.8 to 20, 1 to 20, 2 to 17.5, 3 to 15, 4 to 12.5, 5 to 10, or 7.5 to 9 nm/s, and/or at least 0.01, 0.05, 0.1, 0.2, 0.4, 0.5, 0.6, 0.8, 1.0, 1.5, 1.75, 2, 2.5, 3.33, 3.5, 4, 4.5, 5, 6.5, 7, 7.5, 7.75, 8, 8.25, 8.5, 8.75, 9, or 10 nm/s.

In one embodiment, the method of making the Pd thin film electrode may further comprise a step of cooling the Pd thin film electrode after the contacting. The palladium thin film electrode may be cooled to a temperature between 10 to 45° C., 20 to 40° C., or 25 to 35° C. under an inert gas (such as $N_2$ or Ar) over a time period of 0.5 to 5 h, 0.75 to 4 h, 1 to 3 h, 1.25 to 2.5 h, or 1.5 to 2 h.

In one embodiment, the palladium thin film electrode detects hydrazine in an aqueous sample. Preferably, the palladium thin film electrode is used to detect a concentration of hydrazine, though in some cases, the palladium thin film electrode may only be used to determine whether or not hydrazine is present. Here, the palladium thin film electrode may be immersed in the aqueous sample along with a reference electrode and a counter electrode.

In one embodiment, the aqueous sample may be derived from a body of water such as an ocean, a bay, a river, a spring, a lake, a swamp, or a pond or alternatively, from a treated artificial body of water, such as a pool, fountain, bath, aquarium, or hot tub. The sample may also be water taken from other natural environments such as groundwater (such as a well or an aquifer), rainwater, dew, fog, hot spring, a steam vent, snow, ice, or a geyser. In other embodiments, the aqueous solution may come from processed water or wastewater of industrial process including but not limited to a water treatment plant, a sewage treatment plant, a desalination plant, a manufacturing plant, a chemical plant, a textile plant, a power plant, a gas station, a food processing plant (such as milk or fruit juice), a restaurant, a dry cleaner, or some other place that may be a source of contaminated water. A sample taken from one of the above water sources may be diluted, concentrated, filtered, or may have other compounds added to it, such as salts, acids, or bases.

Preferably the aqueous sample comprises a salt. The salt may comprise at least one cation selected from the group consisting of $K^+$, $Na^+$, $Li^+$, $Cu^{2+}$, $Ag^+$, $Ni^{2+}$, $Co^{2+}$, $Co^{3+}$, $Zn^{2+}$, $Sn^{2+}$, $Pb^{2+}$, $Fe^{2+}$, $Fe^{3+}$, $Cr^{2+}$, and $Cr^{3+}$. The counter ion of the salt may be $SO_4^{2-}$, Br, $NO_3^-$, $OH^-$, $Cl^-$, acetate, or some other anion. The salt may have a concentration of 0.02-1.0 M, preferably 0.05-0.8 M, more preferably 0.08-0.5 M, or about 0.1 M, though in some embodiments, the concentration may be less than 0.02 M or greater than 1.0 M. In a preferred embodiment, the salt is $K_2SO_4$.

In one embodiment, the aqueous sample comprises an inorganic base, such as NaOH, KOH, LiOH, $Mg(OH)_2$, $Ca(OH)_2$, $Ba(OH)_2$, $NH_4OH$, or some other inorganic base. In alternative embodiments, an organic base may be used, such as sodium carbonate or sodium acetate. The inorganic base may have a concentration of 0.02-1.0 M. preferably 0.05-0.8 M, more preferably 0.08-0.5 M.

The aqueous sample may have a total volume of 1 mL-10 L, preferably 5 mL-1 L, more preferably 10 mL-500 mL, even more preferably 15 mL-300 mL.

In one embodiment, for the hydrazine detection, the palladium thin film electrode has a width and/or length in contact with the aqueous sample of 0.1-5.0 cm, preferably 0.3-4.0 cm, more preferably 0.5-3.0. The palladium thin film electrode may have a surface area of 0.5-10 cm$^2$, preferably 0.7-5 cm$^2$, more preferably 1-3 cm$^2$ in contact with the aqueous sample.

The reference electrode may be a standard hydrogen electrode, a normal hydrogen electrode, a reversible hydrogen electrode, a saturated calomel electrode, a silver chloride (Ag/AgCl) electrode, or a dynamic hydrogen electrode. Preferably, the reference electrode is a silver chloride (Ag/AgCl) electrode. In one embodiment, the reference electrode is an Ag/AgCl electrode containing 3 M KCl.

The counter electrode may comprise platinum, gold, or some other metal. Preferably the counter electrode is a platinum wire. The counter electrode may also be called an auxiliary electrode.

For hydrazine detection the palladium thin film electrode is in electrical communication with the reference electrode. After immersing in the aqueous sample, a potential is applied between the reference electrode and the palladium thin film electrode to produce a current within the aqueous sample. The biasing potential may have the waveform of a linear scan voltammetry, a square wave voltammetry, or a cyclic voltammetry. In one embodiment, linear scan voltammetry (LSV) may be applied, using a linear scan of voltage from low to high potential. The potential applied may cause hydrazine oxidation reactions on the Pd surface, which may be noticeable as current peaks. LSV may be used to scan from 0 V to 0.7 V, preferably 0.1 to 0.5 V. A voltage scan rate may be 1-300 mV/s, preferably 2-200 mV/s, more preferably 5-150 mV/s. However, in some embodiments, the voltage scan rate may be slower than 1 mV/s or faster than 300 mV/s. In an alternative embodiment, voltammetry may be used that does not scan linearly through a range of potentials, for instance, different potentials may be applied at discrete steps.

Changes in the current as a result of oxidation of hydrazine may be compared to a correlation chart or a calibration curve to determine the concentration of hydrazine. Here, the correlation chart or calibration curve relates a hydrazine concentration for a particular value of current measured. The correlation chart or calibration curve may be further influenced by other parameters such as voltage, temperature, pH, electrolyte concentration, and other solution conditions. Because of the influence of several solution conditions on the measurement of the hydrazine, the method may comprise a step of measuring standard solutions to construct a correlation chart or calibration curve. This provides a way to better ensure that certain solution conditions do not differ significantly between samples and standard solutions.

In one embodiment, linear scan voltammetry or cyclic voltammetry may be used with an aqueous sample to first identify the location of current peaks as a result of the oxidation. By changing the applied potential in any form of voltammetry, the current may vary based on electrochemical reaction of analyte. As mentioned previously, the current may peak during the voltage scan. For a particular analyte, this peak may occur at a particular voltage or within a smaller range of voltages, and the value of the current at the peak may be linearly dependent on the concentration of analyte. In another embodiment, the current may be influenced by the scan rate.

In one embodiment, the measuring further involves constructing a calibration curve from a current response of two or more standard solutions. This may be considered equivalent to constructing a calibration curve from a correlation chart. Preferably, the standard solutions comprise hydrazine, though in other embodiments, the standard solutions may comprise a different species that has a similar electrochemical response. Preferably the standard solutions produce currents within the linear response range of the graphite electrode, so that a linear calibration curve may be determined to relate current to analyte concentration. Preferably, more than two standard solutions of different concentrations are used, for instance, 3-10 standard solutions, or 4-6 standard solutions. In one embodiment, separate standard solutions may each be prepared and measured one at a time. However, in another embodiment, standard solutions may be measured by a standard addition method, where one volume is measured, and then is mixed with standard solution (usually of a volume 10-1,000 times smaller), while the electrodes are kept in place.

Alternatively, a linear response in current may be obtained by applying a potential at or near the voltage relating to a certain amount of current. In this sense, the measurement technique may be more similar to amperometry. The voltage may be constant or relatively stable, and the current may be measured over time as a chronoamperometric response. Here, a calibration curve may be constructed by measuring a chronoamperometric response while titrating in standard solutions of hydrazine.

In general, where standard solutions are used to construct a linear calibration curve, preferably the standard solutions are within a linear response range of the palladium thin film electrode, so that the linear calibration curve has a correlation coefficient, $R^2$, of at least 0.90, preferably at least 0.95, more preferably at least 0.97, even more preferably at least 0.99.

In some implementations, prior to hydrazine detection, palladium thin film electrode may be treated with an aqueous solution of a strong Arrhenius base to strip away any hydrogen atoms that have complexed to the Pd and reduce the electrocatalytic efficiency of the electrode. The strong Arrhenius base may be, but is not limited to, sodium hydroxide or potassium hydroxide. The concentration of an aqueous solution of sodium hydroxide or potassium hydroxide may be at least 0.05 M, at least 0.75 M, at least 1 M, at least 1.25 M, or at least 1.5 M. The palladium thin film electrode may be treated by the strong Arrhenius base by immersing, spraying, or rinsing.

In one embodiment, using the methods discussed above, the Pd thin film electrode detects hydrazine in an aqueous solution with a limit of detection (LOD) in a range of 1-50 nM, preferably 2-40 nM, more preferably 5-30 nM, even more preferably 8-20 nM, or about 10 nM. In one embodiment, the Pd thin film electrode detects hydrazine in an aqueous solution with a limit of quantification (LOQ) in a range of 1-50 nM, preferably 15-45 nM, more preferably 25-35 nM, or about 33 nM. However, in other embodiments, the LOD and/or LOQ may be less than 1 nM or greater than 50 nM.

In one embodiment, the Pd thin film electrode detects hydrazine in an aqueous solution with a linear chronoamperometric response over a hydrazine concentration of 0.5-350 µM, preferably 0.8-250 µM, more preferably 1-180 µM. In this embodiment, the palladium thin film electrode may have a sensitivity of 0.1-100 $\mu A \cdot mM^{-1} \cdot cm^{-2}$, preferably 1-10 $\mu A \cdot mM^{-1} \cdot cm^{-2}$, or about 3 $\mu A \cdot mM^{-1} \cdot cm^{-2}$.

In one embodiment, the Pd thin film electrode may detect other hydrazine-related compounds and drugs, including but not limited to 1,2-dimethylhydrazine, 1,1-dimethylhydrazine, 4-phenylthiosemicarbazide, acylhydrazine, adipic acid dihydrazide (ADH), agaritine, benmoxin, cadralazine, carbazide, carbidopa, carbohydrazide, daminozide, dihydralazine 2,4-dinitrophenylhydrazine (DNPH), endralazine, gyromitrin, 5,5'-hydrazinebistetrazole (HBT), hydralazine, hydrazide, hydrazine, iproclozide, iproniazid, isocarboxazid, isoniazid, mebanazine, metfendrazine, monomethylhydrazine (MMH), nialamide, octamoxin, phenylethylidenehydrazine (PEH), phenelzine, pheniprazine, phenoxypropazine, phenylhydrazine, pildralazine, pimagedine, pivalylbenzhydrazine, procarbazine, safrazine, semicarbazide, semicarbazone, and/or tetrafluorohydrazine. In other embodiments, the Pd thin film electrode may be used to measure or detect other compounds, pharmaceuticals, metabolites, or biological molecules. On the other hand, the palladium thin film electrode may be able to measure hydrazine or hydrazine-related compounds in the presence of certain other compounds such as ascorbic acid, uric acid, ammonia, glucose, caffeine, n-butylamine, adenosine, cytosine, guanine, thymine, hydroxylamine, L-arginine, DMF, and/or ethylenediamine without undue interference.

The examples below are intended to further illustrate protocols for preparing and characterizing the palladium thin film electrode, and using to detect hydrazine, and are not intended to limit the scope of the claims.

Example 1

Experimental

Methods and Chemicals

FTO electrodes (6-8 $\Omega$/sq) were purchased from Geomatec, Japan. Palladium acetylacetonate ($Pd(C_5H_7O_2)_2$), hydrazine, ethylene diamine, dimethyl sulfoxide, and toluene, were all received from Sigma-Aldrich. Deionized water (resistivity 18.2 M$\Omega$·cm at 25° C.) was used for aqueous solutions' preparation.

Electrode Fabrication Process

Palladium thin film electrodes were produced using AACVD method. The design and assembly of AACVD setup is already reported in literature. See M. A. Ehsan, R. Naeem, H. Khaledi, M. Sohail, A. H. Saeed, M. Mazhar *Dalton Transactions*, 2016. 45, 10222-10232-incorporated herein by reference in its entirety. The precursor solution was synthesized by dissolving palladium acetylacetone $Pd(acac)_2$ (100 mg, 0.328 mM) compound in toluene (10 mL), and the resultant transparent yellow solution was used for growth of palladium thin films by AACVD. The glass substrates (i.e., FTO and plain glass) of dimensions 1.0×2.0 $cm^2$ (W×L) were cleaned with soapy water, acetone, and isopropanol and were then kept to air dry prior to deposition. For each deposition experiment, the substrate was aligned horizontally inside the reactor tube, pre-heated up to the deposition temperature (475° C.), kept there for 10 minutes to make the temperature equilibrated, and then the deposition process was started. The aerosol mist from $Pd(acac)_2$ solution was generated using piezoelectric ultrasonic humidifier and the aerosol was injected to the reactor tube carried by a stream of nitrogen ($N_2$) gas at a rate of 150 $cm^3$/min. The deposition experiments were continued for 30 min. The waste exhaust of the precursor mist was all vented into a fume hood. After deposition, the films were allowed to cool to room temperature under a continuous flow of $N_2$ gas. The resulting film electrodes were uniform, shiny, greyish in colour, and stable in open air. The adhesion property of palladium thin film was verified by the "SCOTCH tape test," where the thin film layers were found to strongly intact with the FTO substrate. Multiple films of all samples were synthesized to determine the reproducibly of the process.

Film Electrode Alaysis

X-ray diffraction (XRD) patterns of palladium film were recorded using Rigaku MiniFlex X-ray diffiactometer (Japan) with Cu K$\beta$1 radiation ($\gamma$=0.15416 nm), a tube current of 10 mA, and an accelerating voltage of 30 kV. Scanning electron microscope images of the film electrodes were analyzed by a field emission scanning electron microscope (FESEM, LYRA3, Tescan, Czech Republic) at an accelerating voltage of 20 kV. The elemental stoichiometry and composition of film electrodes were investigated by Energy dispersive X-ray (EDX, INCA ENERGY 200, Oxford Inst.) spectroscopy. X-ray photoelectron spectroscopy (XPS) experiments were performed in a Thermos Scientific ESCALAB 250Xi spectrometer equipped with a monochromatic Al K$\alpha$ (1486.6 eV) X-ray source, having a resolution of 0.5 eV. During the XPS characterization, the ambient conditions of temperature were maintained while the pressure was controlled at 5×10$^{-10}$ mbar. The spectra were referenced with adventitious C 1 s peak at 284.5 eV.

Electrochemical Measurements

All electrochemical experiments were performed with p-AutoLab PGSTAT101, in a conventional three electrode setup. Bare, modified FTO electrodes, or Pd-thin film/FTO electrodes were used as the working electrodes, Ag/AgCl/3M KCl as the reference electrode, and a platinum wire was used as the counter electrode. 0.1 M potassium sulfate was used as a sensing medium in the entire electroanalysis after 10 min of nitrogen purging in the solution. All electrochemical measurements were performed at room temperature.

Example 2

Results and Discussion
Characterization of Pd Thin Film Electrodes

Palladium thin films were developed on plain and FTO glass substrates at 475° C., consuming the toluene solution of precursor $Pd(acac)_2$ in AACVD and using $N_2$ as a carrier gas. In order to avoid the crystalline contributions from the FTO substrate, films deposited on plain glass substrates were examined by XRD analysis. FIG. 1 represents the XRD pattern of film which clearly identifies the deposit as metallic palladium demonstrated by the reflections in the (111), (200), (220), (311), and (222) planes at 2$\theta$ values of 40.0°, 46.5°, 68.0°, 81.0°, and 86.4°, respectively, corresponding well with the standard pattern (BD-01-088-2335) and crystallized in a cubic crystal structure. It is worth mentioning that Pd films are produced under the flow of $N_2$ gas (99.999% pure) and without incorporating any reducing agent or hydrogen gas during the deposition process. This observation is in contrast to previous CVD reports where the usage of $H_2$ gas was necessary to covert Pd(II) ions to metallic Pd. See W. Lin, T. H. Warren, R. G. Nuzzo, G. S. Girolami, *Journal of the American Chemical Society* 1993, 115, 11644-11645, incorporated herein by reference in its entirety. Further, XRD results are in agreement with previous palladium thin films fabricated onto stainless steel substrates by electrochemical methods in a buffer solution. See H. Heydari, A. Abdolmaleki, M. B. Gholivand, *Ciência e Natura* 2015, 37, 23-33, incorporated herein by reference in its entirety. Moreover, no preferred orientations were observed, and it was found that the pure Pd films were grown regardless of the substrate effect whether it was glass or stainless steel, indicating that the substrates had no influence on the crystallographic phase. Although the precursor $Pd(acac)_2$ contained oxygen atoms, its thermal decomposition under inert conditions of AACVD completely eliminated the organic moiety in form of $CO_2$ and $H_2O$. Pd-oxide formation was not observed through the XRD results. No crystalline side product such as a formation of palladium oxide was observed, and all crystalline peaks were completely in agreement with pure Pd.

Figure 2A:
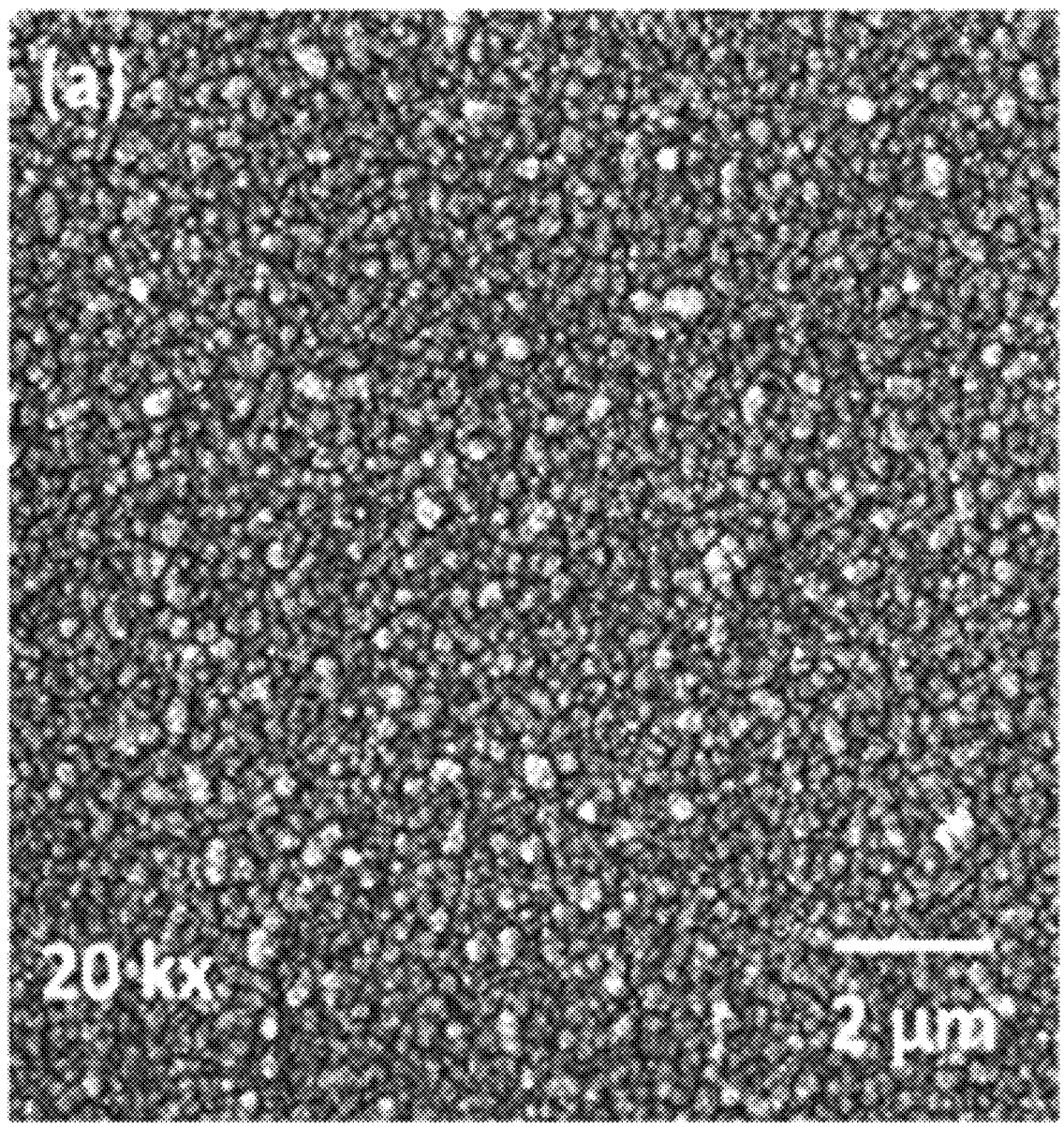
FIG. 2A is a low resolution FESEM surface micrograph of palladium thin film deposited on an FTO substrate.
Figure 2B:
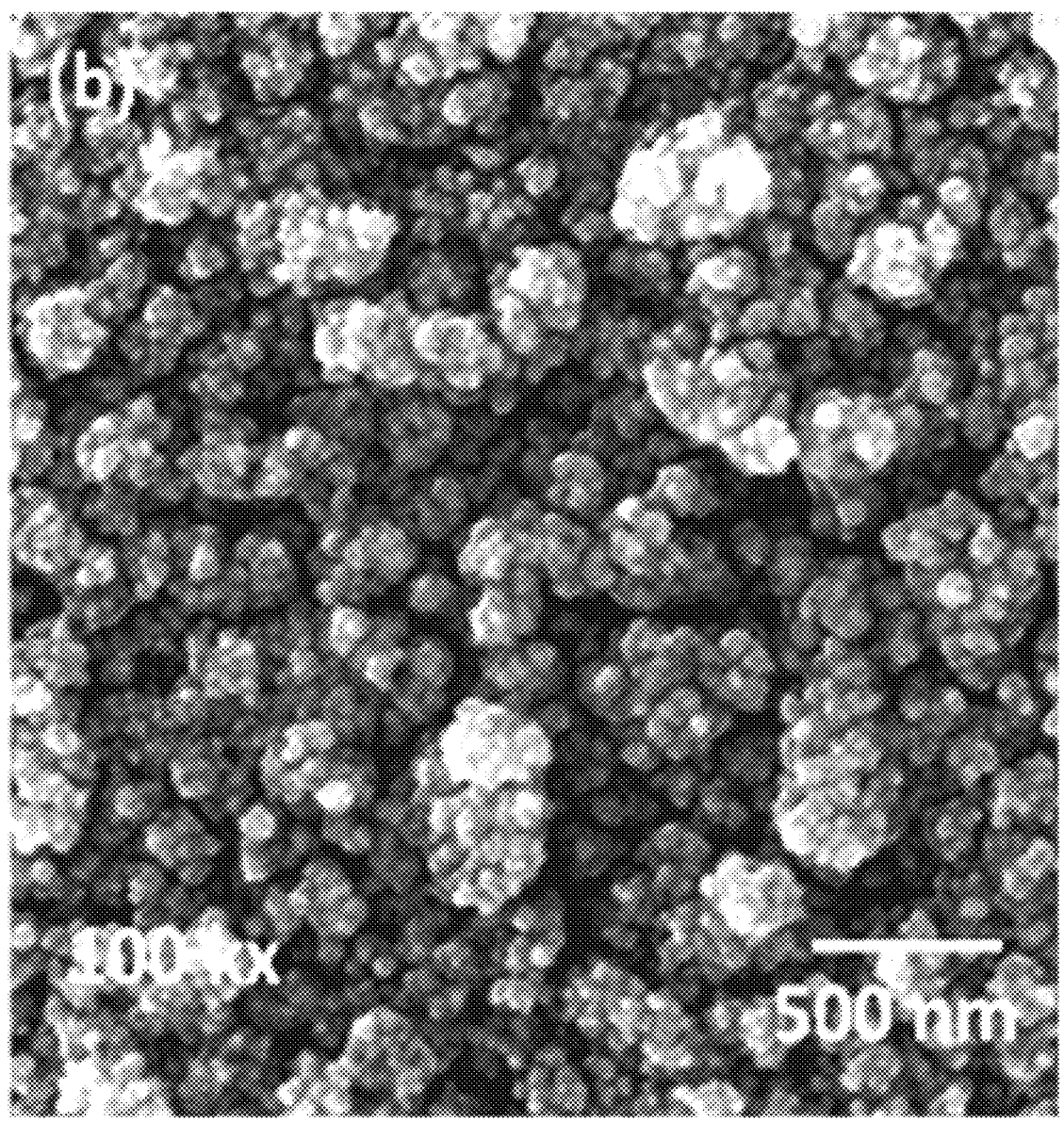
FIG. 2B is a high resolution view of the palladium thin film sample of FIG. 2A.
Figure 2C:
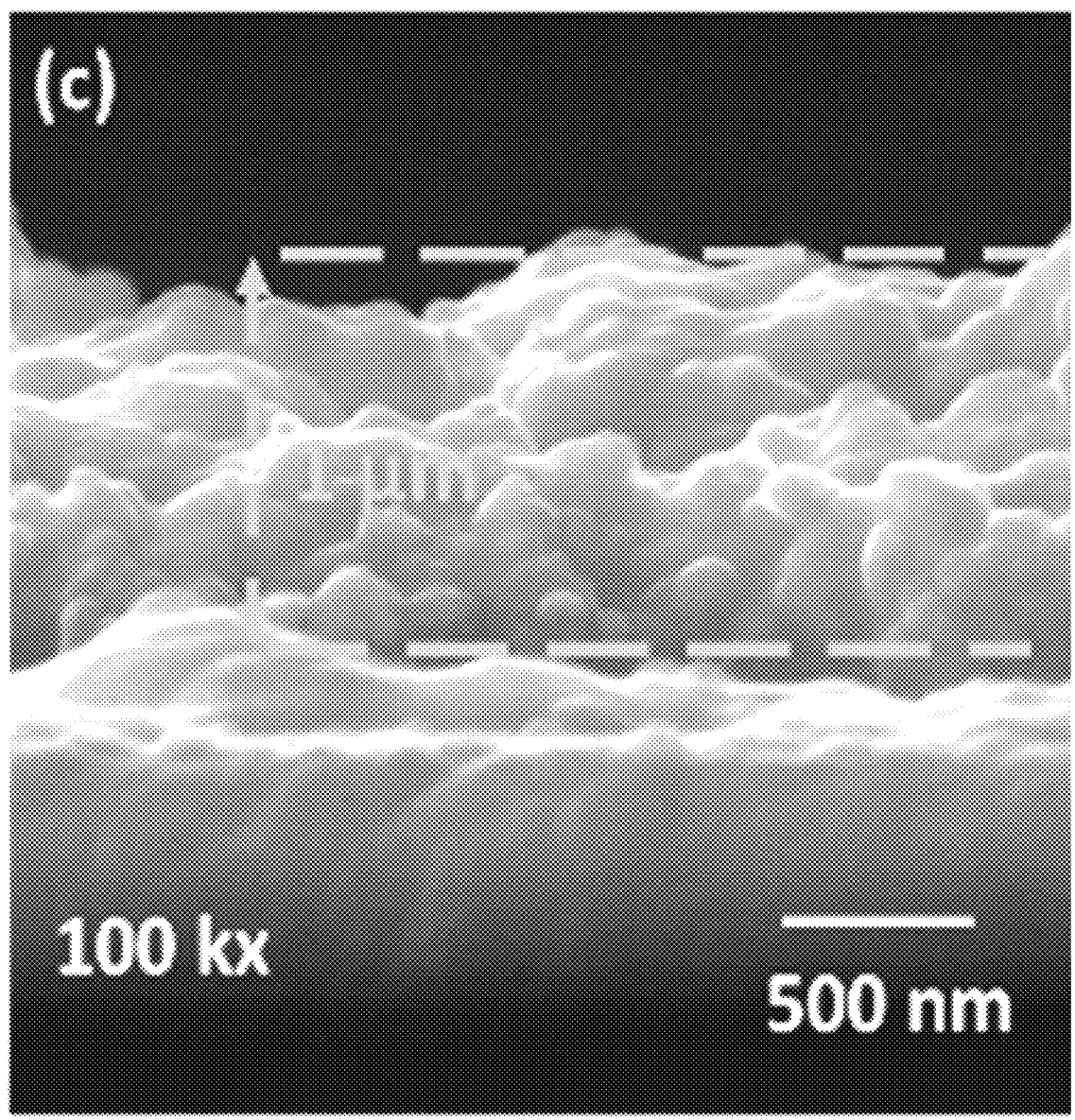
FIG. 2C is a cross sectional view of FIG. 2B.

FIGS. 2A-C display the surface and cross-sectional SEM micrographs of deposited palladium film. The low resolution surface imaging (FIG. 2A) indicates the uniform layer of Pd on the substrate surface. The entire surface of the substrate was covered and crack formation or Pd-less spots were not observed (FIG. 2A). The corresponding high magnification SEM image presented in FIG. 2B indicates that deposited Pd nanostructures attained a cauliflower shape with particle sizes varying from 50 nm to several hundreds of nanometers. Each particle of such structure was further covered by smaller particles of similar shape (FIG. 2B). The smallest particles on the surface layer might be in the nanometer range. These rough and porous nanostructures increased the active surface area of the electrode when compared to an electrode with a smooth surface having the same geometric shape. FIG. 2C shows that the cross-section of a palladium film and the thicknesses of a Pd layer was estimated to be ~1 µm.

Figure 3A:
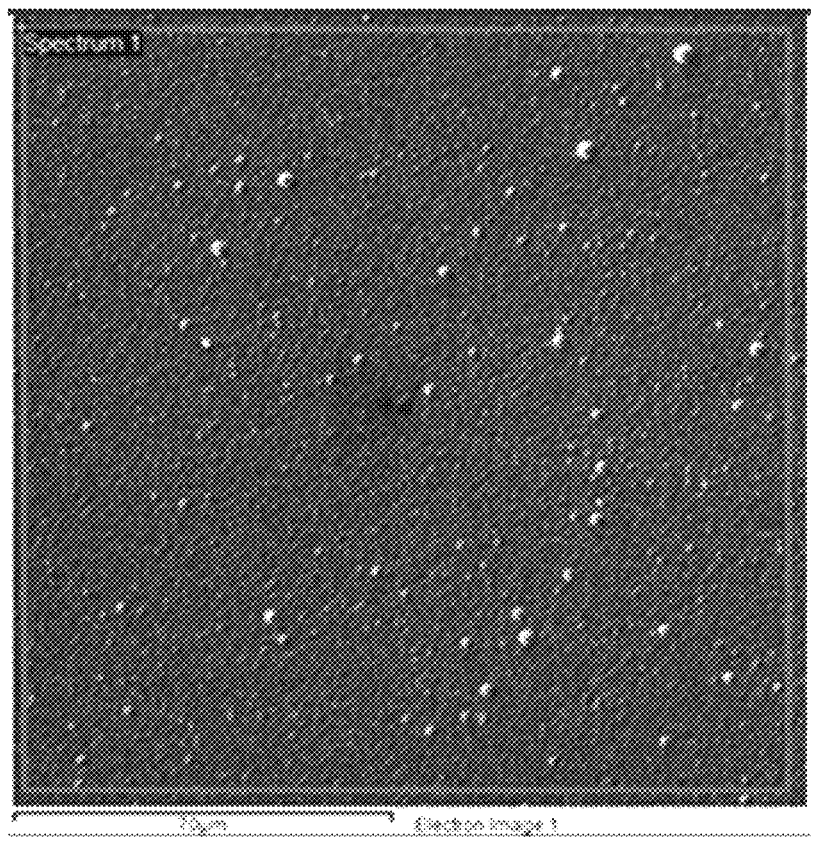
FIG. 3A is a SEM image of a palladium film deposited on FTO substrate at 475° C. via AACVD and selected for EDX spectrum analysis.
Figure 3B:
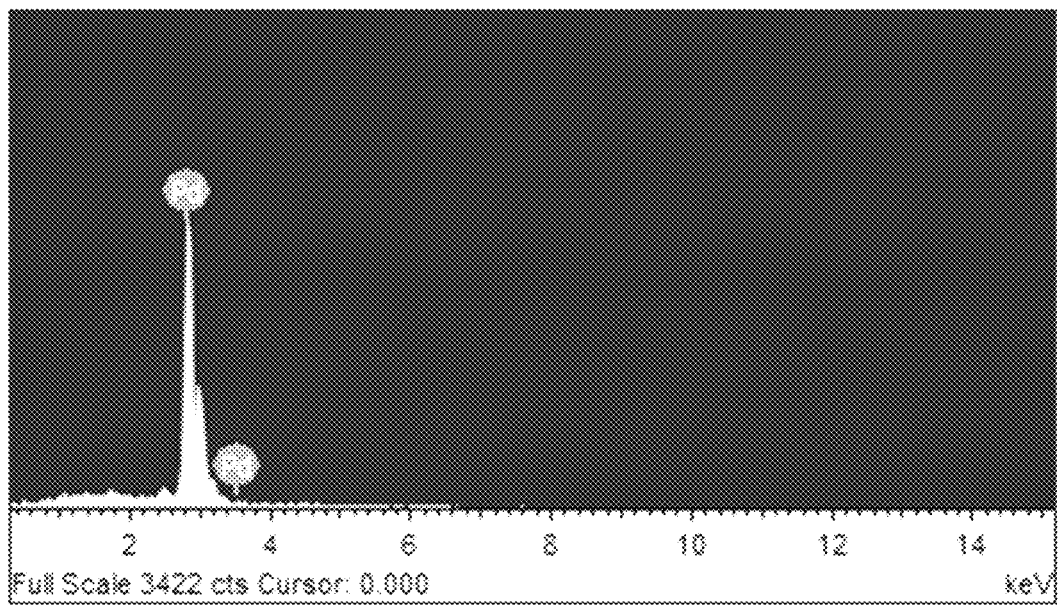
FIG. 3B is the resulting EDX spectrum of the palladium film of FIG. 3A.

EDX analysis was conducted to verify the presence of elemental palladium in the film. FIG. 3B reveals the EDX spectrum of the region at FIG. 3A. The EDX spectrum clearly shows that the signal peaks originated only from elemental Pd. The expected Sn and O signals from the FTO substrate did not appear due to the thick layer of Pd. Interestingly, no carbonaceous signals are found, which indicates the clean thermal decomposition of precursor $Pd(acac)_2$ during AACVD process and further verifies the production of high purity Pd films.

Figure 4:
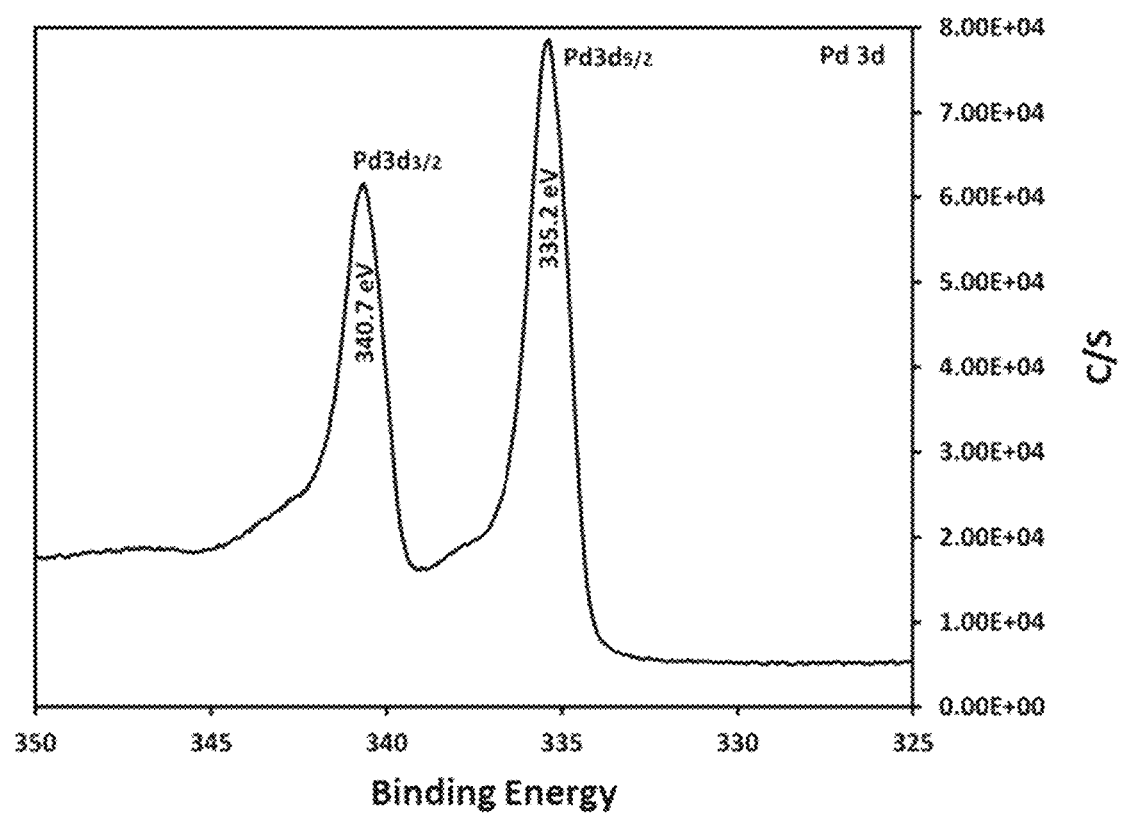
FIG. 4 is a high resolution XPS of palladium thin film showing binding energies for the $Pd^0$ state.

X-ray photoelectron spectroscopy (XPS) was used to determine the oxidation state of the Pd deposit. The high resolution XPS spectrum of the Pd 3d revealed two characteristic peaks at a binding energy of 335.2 and 340.7 eV, corresponding to Pd $3d_{5/2}$ and Pd $3d_{3/2}$, respectively, (FIG. 4). This result indicated that Pd exists in oxidation state (0) and confirmed the preparation of pure Pd thin films. See S. Yang, J. Dong, Z. Yao, C. Shen, X. Shi, Y. Tian, S. Lin, X. Zhang, *Scientific reports* 2014, 4, 4501; Z. Li, J. Li, J. Liu, Z. Zhao, C. Xia, F. Li, *Chem Cat Chem* 2014, 6, 1333-1339, incorporated herein by reference in its entirety. Usually, the formation of palladium oxide traces could be noticed by the presence of shoulder peaks on 3d peaks at a slightly higher binding energy than Pd(0). See M. S. Saifullah, R. Ganesan, S. H. Lim, H. Hussain, H. Y. Low, *RSC Advances* 2016, 6, 21940-21947, incorporated herein by reference in its entirety. However, these characteristic shoulders did not appear in these examples. Thus, the possibility of oxide formation was eliminated in the deposited films. The XPS results were in line with XRD and EDX analysis, further validating the growth of pure metallic palladium films.

Electrochemical Sensing of Hydrazine at Pd-Thin Film/FTO Electrode

Figure 5:
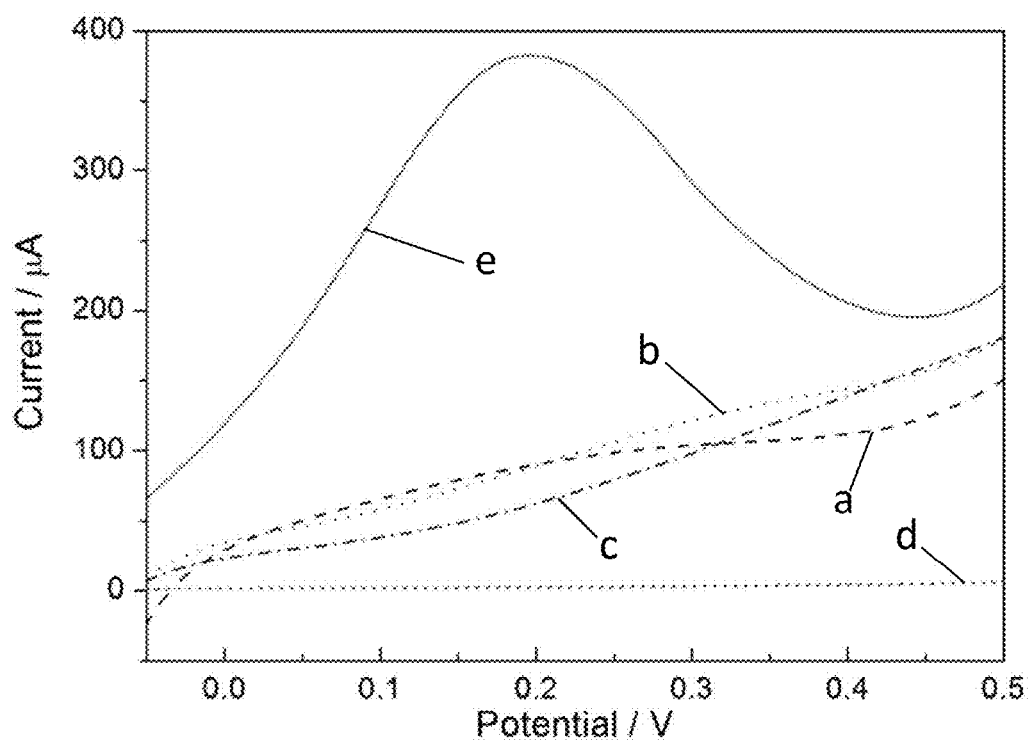
FIG. 5 is an interference study of nanostructured Pd film electrode in 0.1M $K_2SO_4$ in the presence of 120 μM (a) ascorbic acid, (b) ethylene diamine, (c) DMF+ethylene diamine, (d) hydrazine response with Pd-wire and (e) hydrazine with synthesized Pd-thin film at 100 mV/s.

FIG. 5 presents electrochemical investigations with linear scan voltammetry (LSV). When 120 µM of hydrazine was present in a measurement solution of 0.1 M $K_2SO_4$, a strong oxidation peak was observed for hydrazine at Ep 0.195 V (curve "e" in FIG. 5) using a nanostructured Pd-thin film/FTO working electrode. Compared to the Pd-thin film/FTO electrode, commercially available Pd-wire did not produce any response for hydrazine in the tested potential window (curve "d" in FIG. 5). The appearance of a strong oxidation peak at as low as 0.195 V with the nanostructured Pd-thin film/FTO electrode could be a result of the rough and porous nanostructure with superior catalytic activity of Pd films. Further, the presence of other electroactive interferences including ascorbic acid (120 µM), ethylene diamine (120 µM), and DMF+ethylene diamine (120 µM each), did not show any response in the potential window used for hydrazine(curves "a," "b," and "c" in FIG. 5). Further, the presence of these interfering species in the measuring solution did not affect the current response for hydrazine. Hence, the nanostructured Pd-thin film/FTO electrode showed sensitive and selective response towards hydrazine oxidation.

Figure 6A:
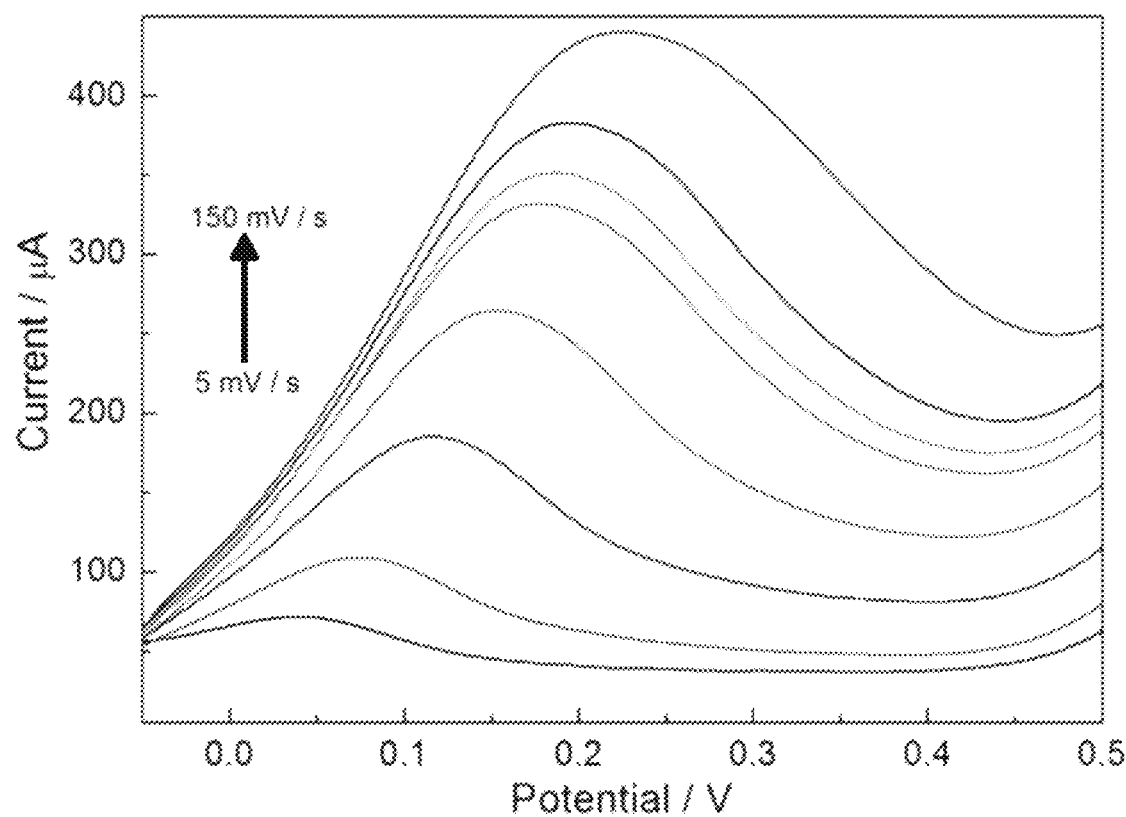
FIG. 6A is a LSV measured in 120 μM hydrazine in 0.1 M $K_2SO_4$ at different scan rates on nanostructured Pd-thin film/FTO electrode.
Figure 6B:
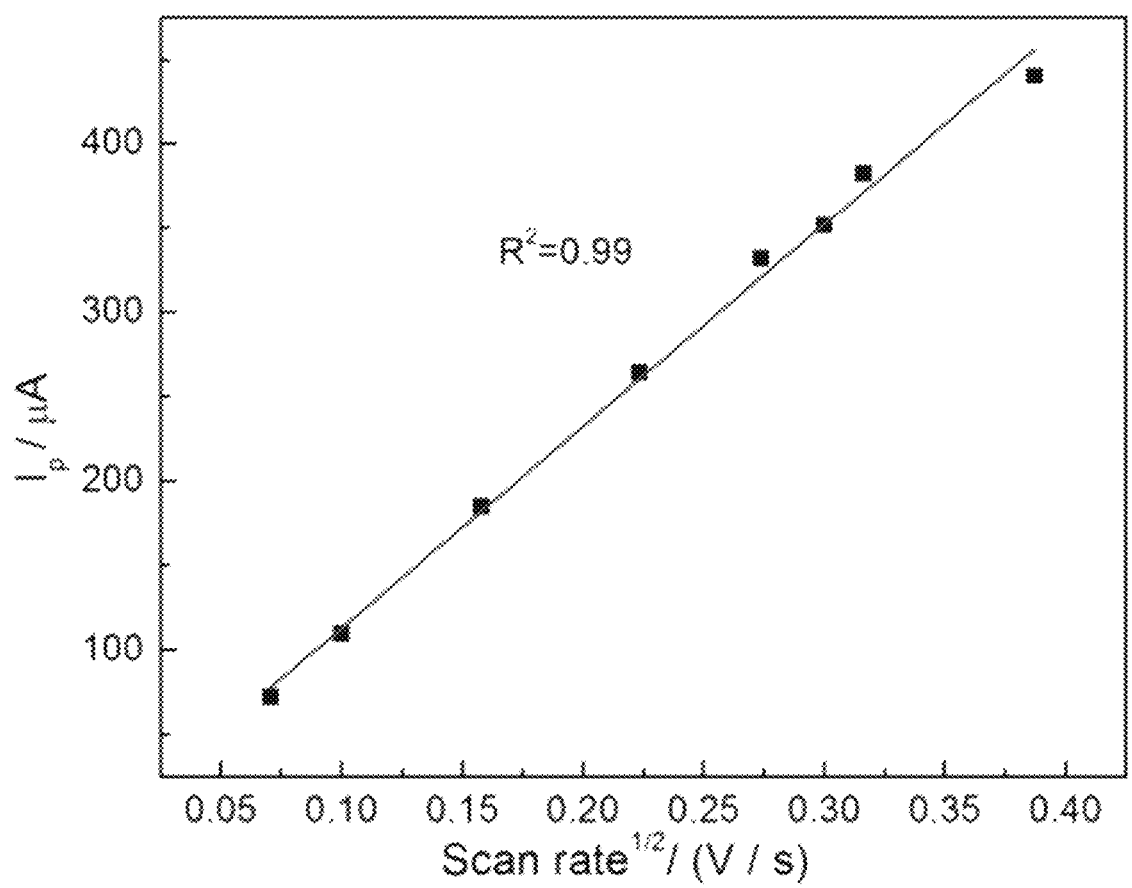
FIG. 6B is a plot of mass activity vs. the square root of the scan rate ($v^{1/2}$).
Figure 11:
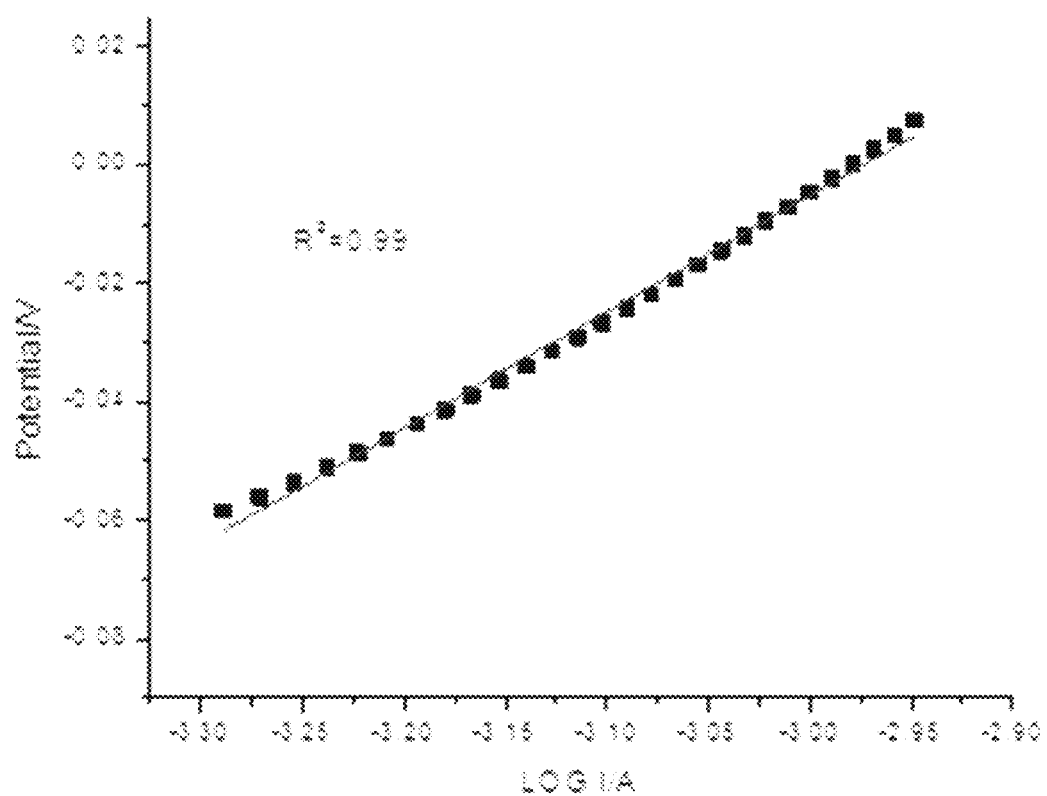
FIG. 11 is a Tafel slope (195 mV (decade A)$^{-1}$) with Pd/FTO electrode in 0.1 M $K_2SO_4$ and 120 μM hydrazine at scan rate=50 mV/s, T=25° C., α=0.7.

Hydrazine oxidation was investigated for nanostructured Pd-thin film/FTO electrode using LSV at different scan rates (FIGS. 6A-B). It was observed that with the change in scan rate, both peak current and peak potential were changed (FIG. 6A). The oxidation peak potentials shifted towards higher values with increasing scan rate, indicating the structural change in the electrochemically formed diffusion film at the electrode surface. Meanwhile, the rise in the peak current for hydrazine oxidation with increase in the scan rate indicated progressive enrichment with accessible electroactive species on or near the electrode surface. See M. D. Garcia, M. L. Marcos, J. G. Velasco, *Electroanalysis* 1996, 8, 267-273, incorporated herein by reference in its entirety. When the number of electrons transferred in the rate determining step for hydrazine oxidation was considered 1, the electron transfer coefficient was found to be 0.7 (FIG. 11). See J. Li, X. Lin, *Sensors and Actuators B: Chemical* 2007, 126, 527-535, incorporated herein by reference in its entirety. Linear plots between mass activities versus the square root of the scan rate ($v^{1/2}$) obtained by applying the Randles-Sevcik equation, shown in FIG. 6B, indicating that the hydrazine oxidation reaction might be a diffusion-controlled process. See M. D. Garcia et al., incorporated herein by reference in its entirety.

Figure 12:
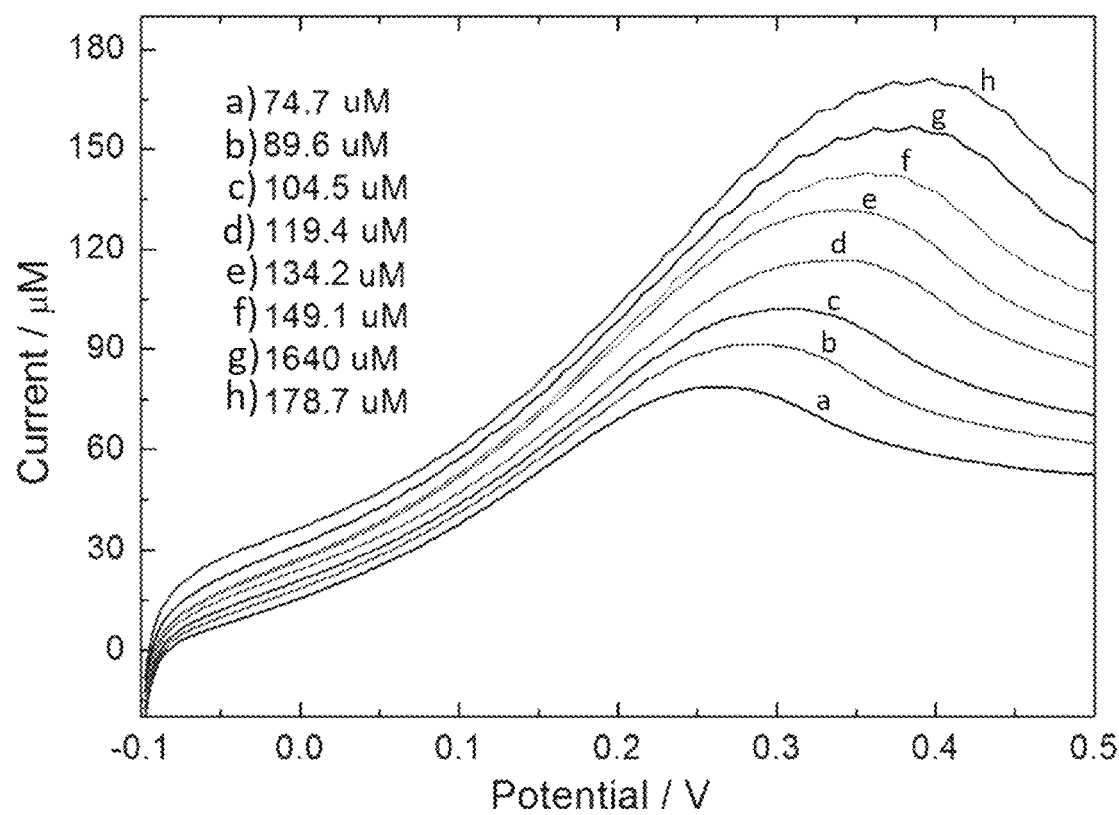
FIG. 12 shows linear sweep voltammograms (scan rate 50 mV/s) recorded using Pd/FTO electrode in 0.1 M $K_2SO_4$ at various concentrations of hydrazine.
Figure 13:
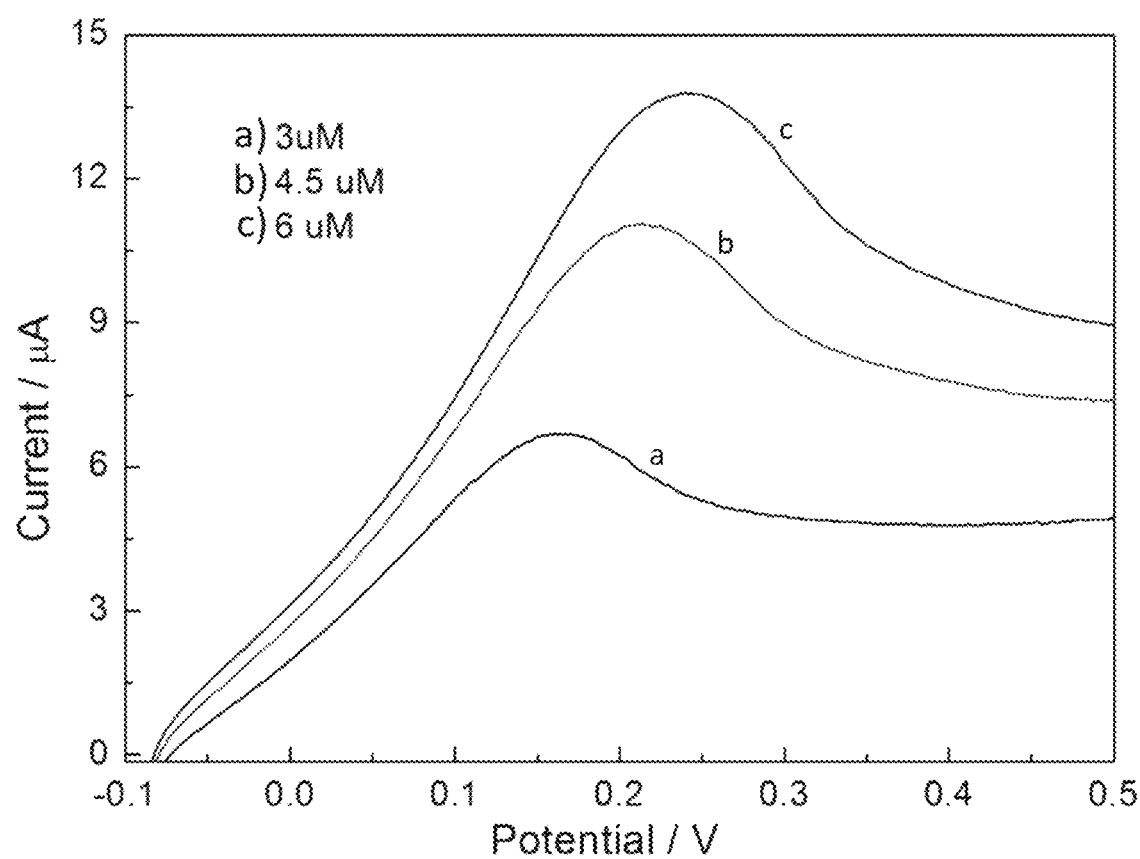
FIG. 13 shows additional linear sweep voltammograms (scan rate 50 mV/s) recorded using Pd/FTO electrode in 0.1 M $K_2SO_4$ at additional concentrations of hydrazine.
Figure 14:
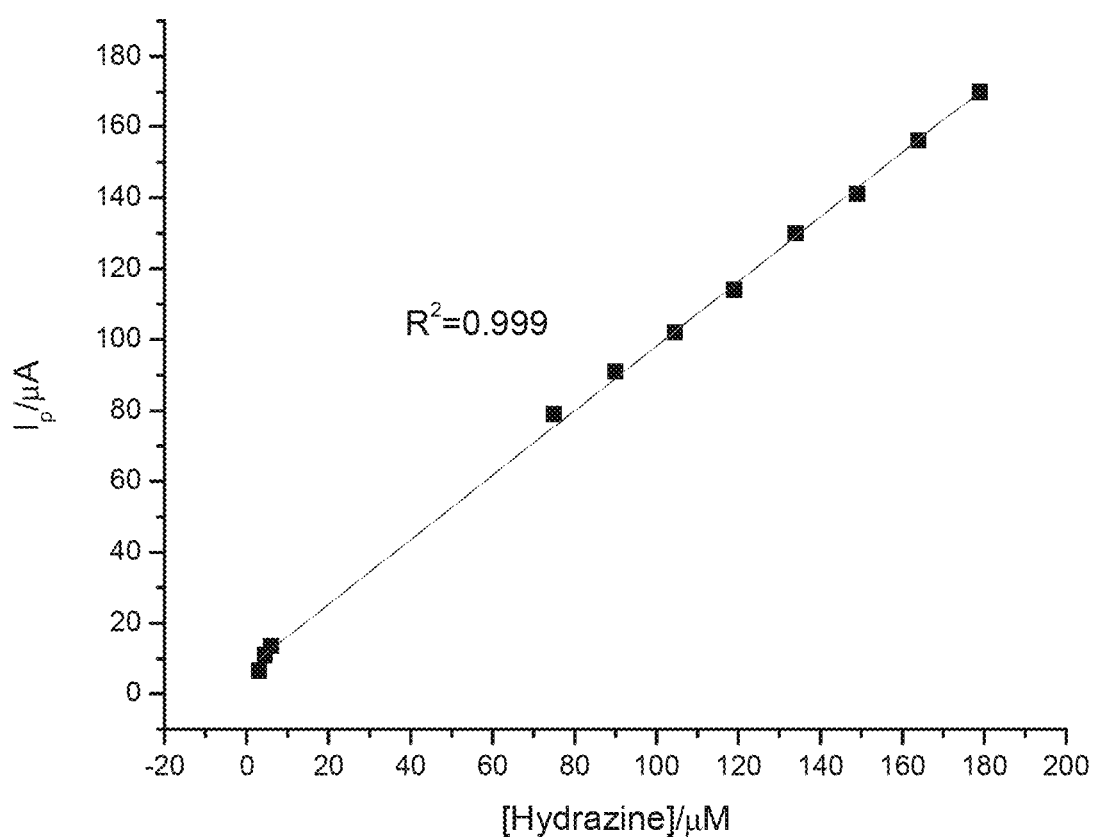
FIG. 14 shows the linear relationship between peak current (μA) and concentration (μM) of hydrazine.
Figure 15:
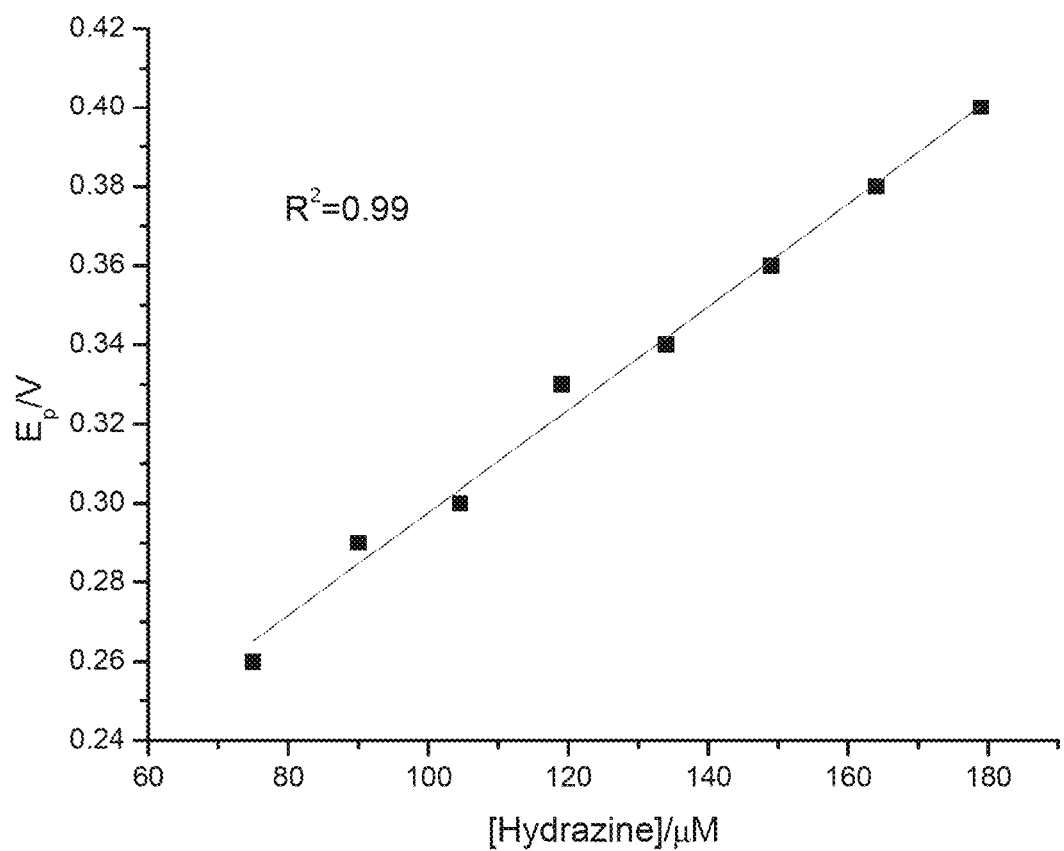
FIG. 15 is a plot showing the changes in $E_p$ (potential for maximum oxidation peak current) with the change in hydrazine concentration.
Figure 16:
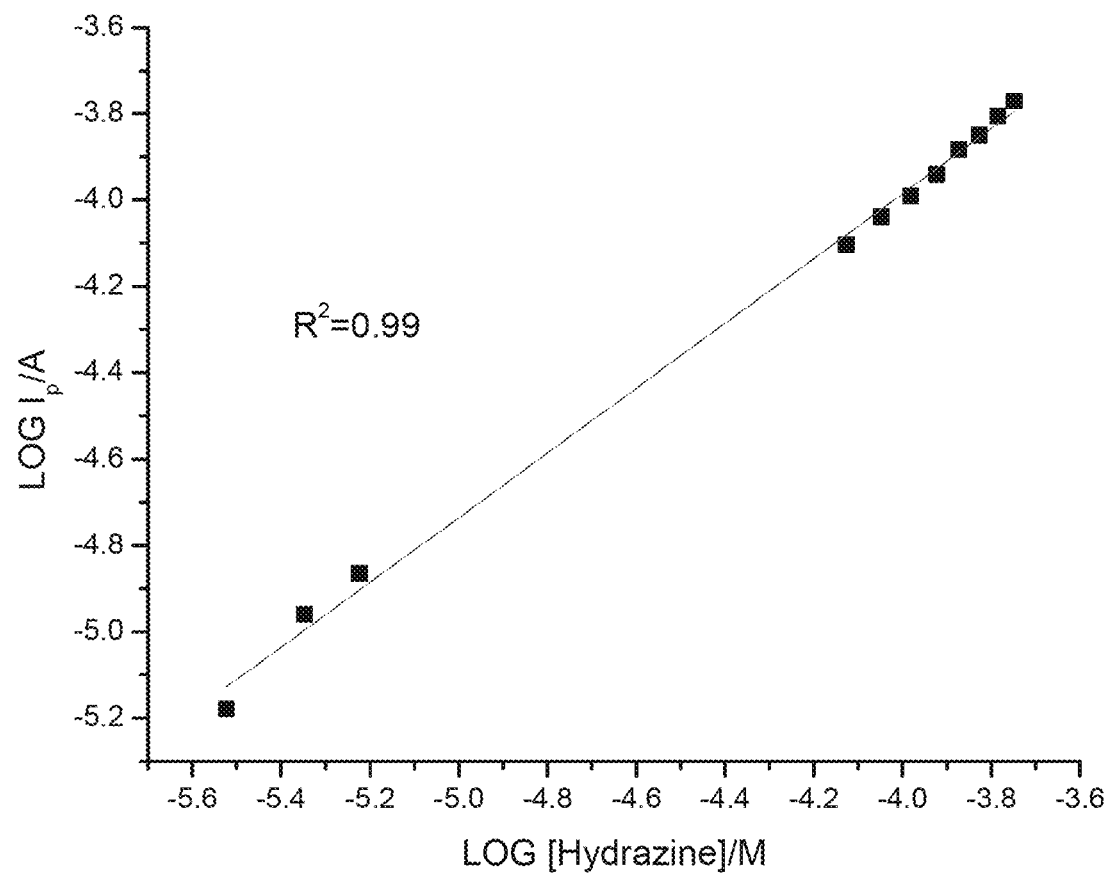
FIG. 16 is a plot showing change in log of $I_p$ with log of hydrazine concentration.
Figure 17:
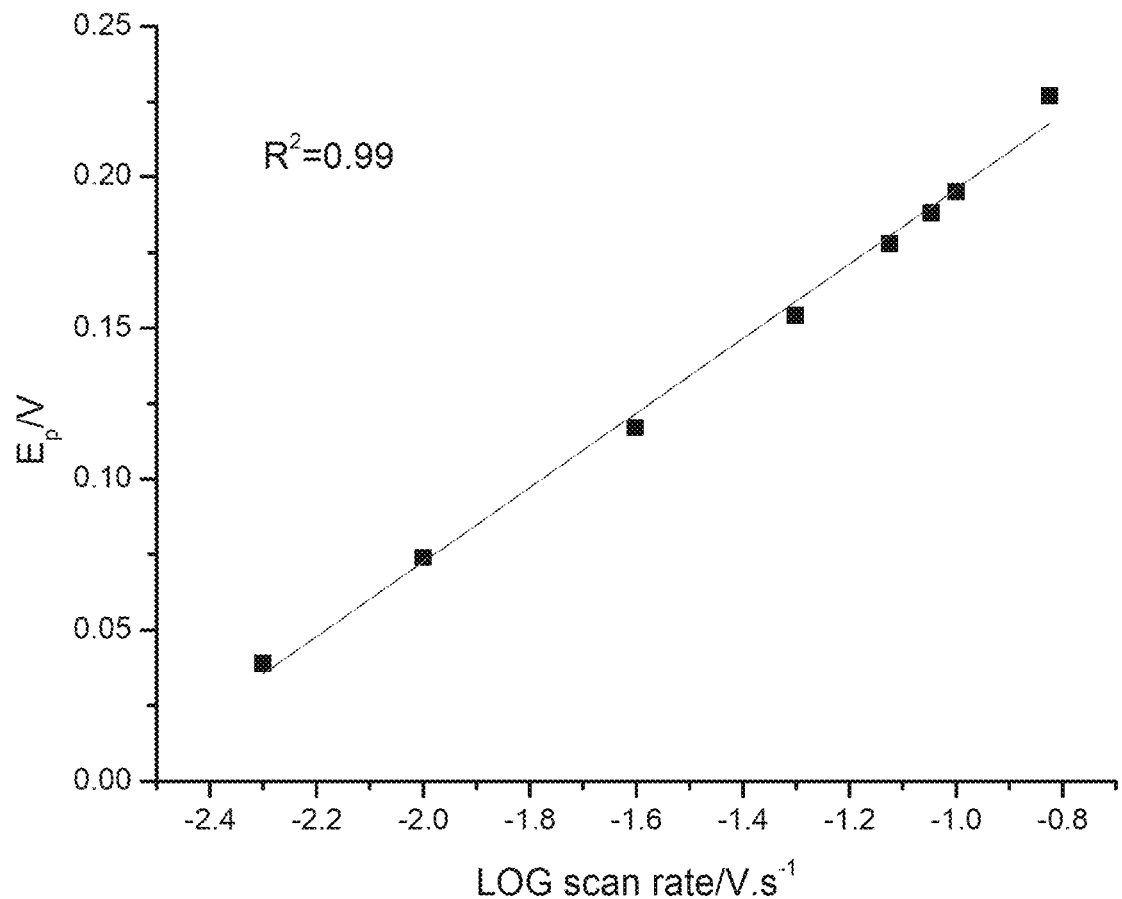
FIG. 17 is a plot of $E_p$ vs. Log (v).

The LSV curves obtained for different concentrations of hydrazine in the measurement solution are presented in FIGS. 12 and 13. The dynamic linear concentration range through LSV with the Pd-thin film/FTO electrode was found from concentrations of 1 to 179 µM (FIG. 14). The plots between potential for maximum oxidation peak current change ($E_p$) with change in hydrazine concentration (FIG. 15) and variation in log of maximum anodic peak current ($I_p$) with log of hydrazine concentrations were also plotted (FIG. 16). A linear increase in oxidation peak current and corresponding peak potential was observed with the increase in hydrazine concentration. The change in $E_p$ with the log of hydrazine concentration (log CHz) was 357 mV per decade. Hydrazine concentration could also be quantitatively determined by using both of these plots. FIG. 17 shows a plot between $E$, and the log of the scan rate (log v).

Figure 7A:
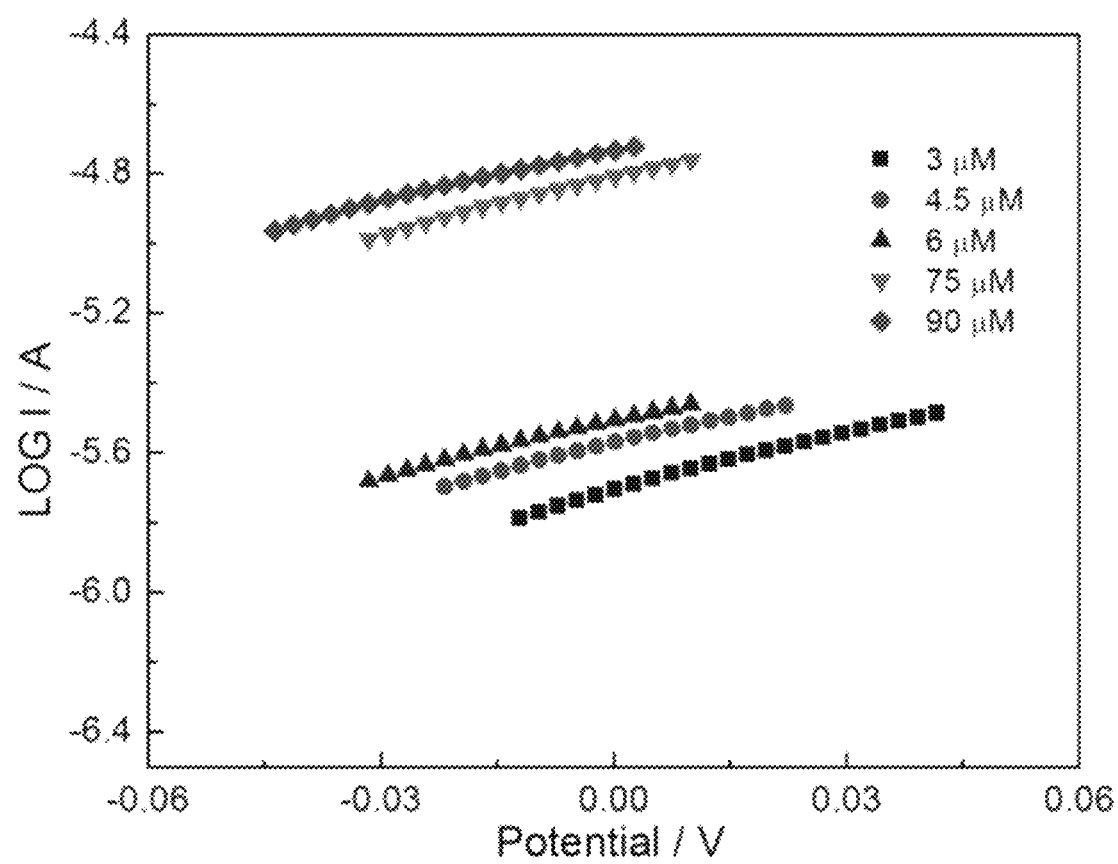
FIG. 7A shows the effect of hydrazine concentration on Tafel slopes below 100 μM (190 mV (decade A)$^{-1}$) with nanostructured Pd electrode in 0.1 M $K_2SO_4$, with a scan rate of 50 mV/s and a temperature of 25° C.
Figure 7B:
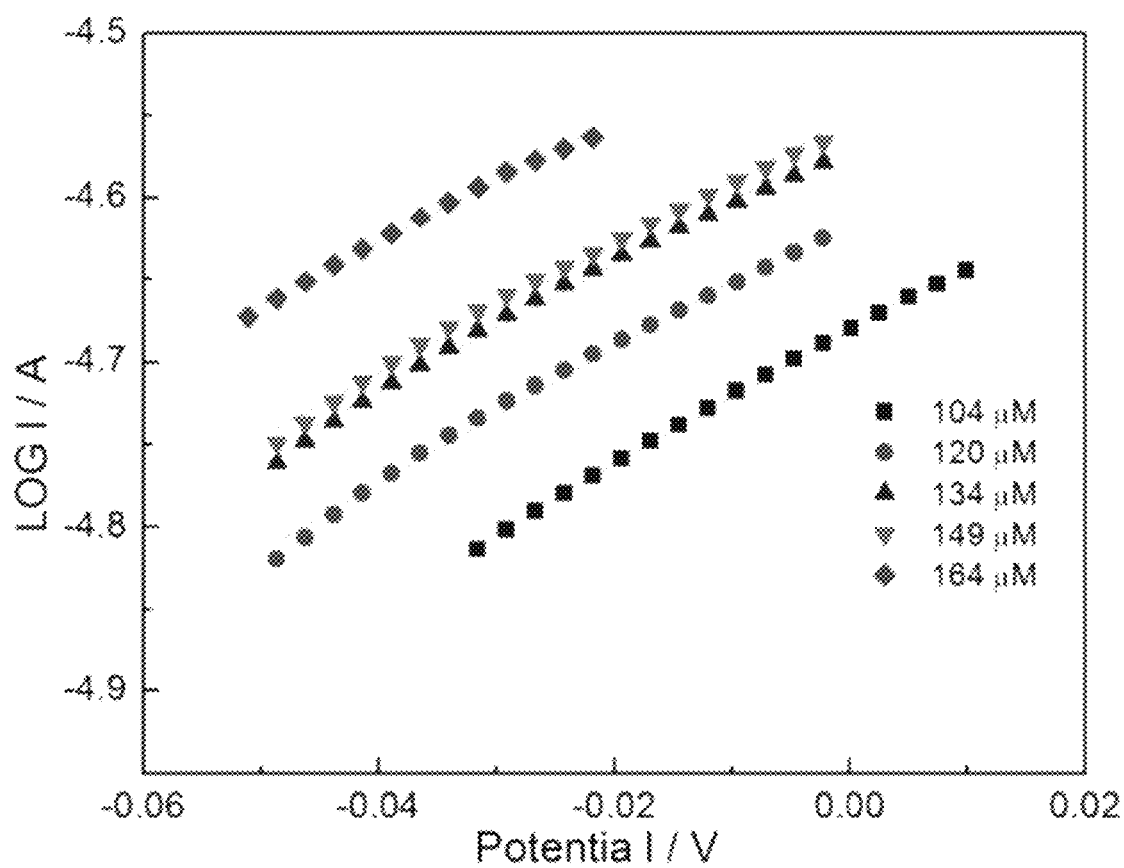
FIG. 7B shows the effect of hydrazine concentration on Tafel slopes above 100 μM (256 mV (decade A)$^{-1}$) with nanostructured Pd electrode in 0.1 M $K_2SO_4$, with a scan rate of 50 mV/s and a temperature of 25° C.

Further, Tafel slopes were plotted to determine the mechanism of the hydrazine oxidation. Tafel plots between potential (below peak potential) and corresponding currents for different hydrazine concentrations are shown in FIGS. 7A and 7B. Based on two different Tafel slopes, there are two linear hydrazine concentration ranges, i.e. below and above 100 µM. This indicates a concentration dependent hydrazine oxidation mechanism which is different than previous reported work in which Tafel slope remained constant at all concentrations. See M. Sohail et al., incorporated herein by reference in its entirety.

Figure 8A:
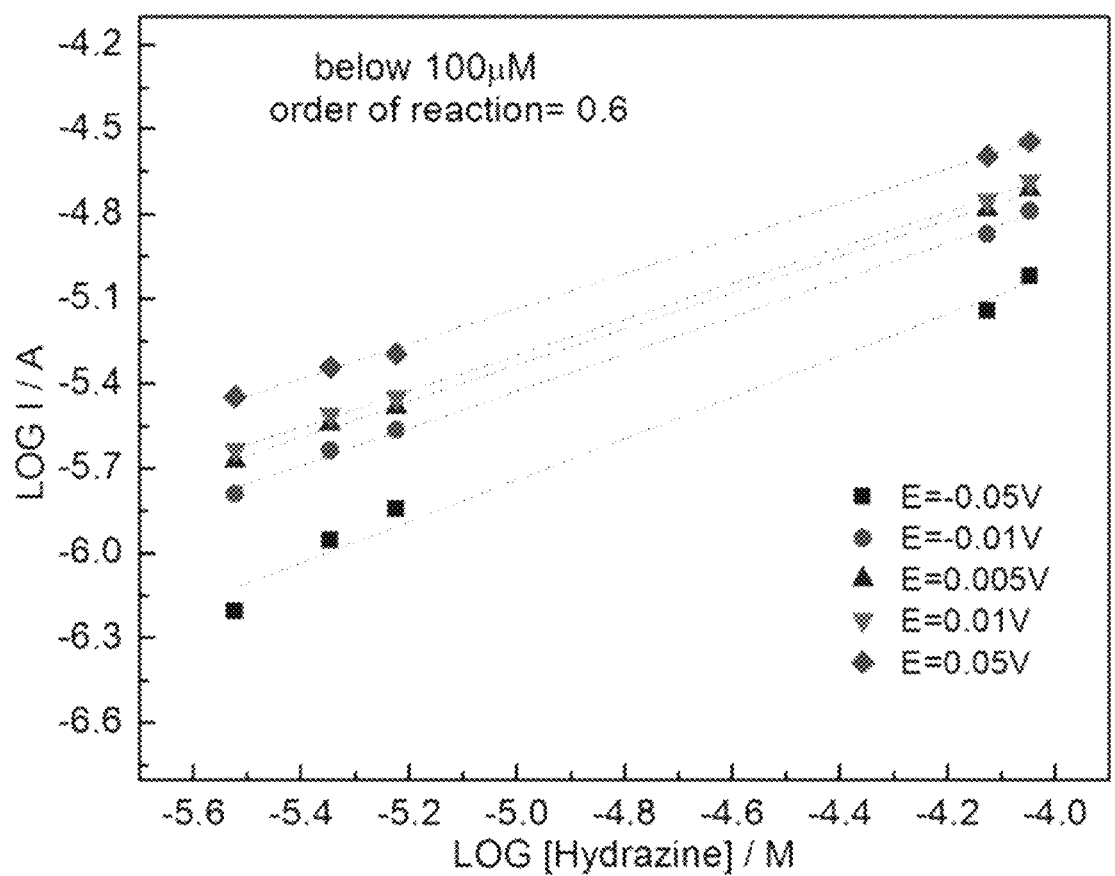
FIG. 8A shows a plot of Log I vs Log [Hydrazine] (below 100 μM) at different potential values (below peak potential), in 0.1 M $K_2SO_4$, with a scan rate of 50 mV/s and a temperature of 25° C.
Figure 8B:
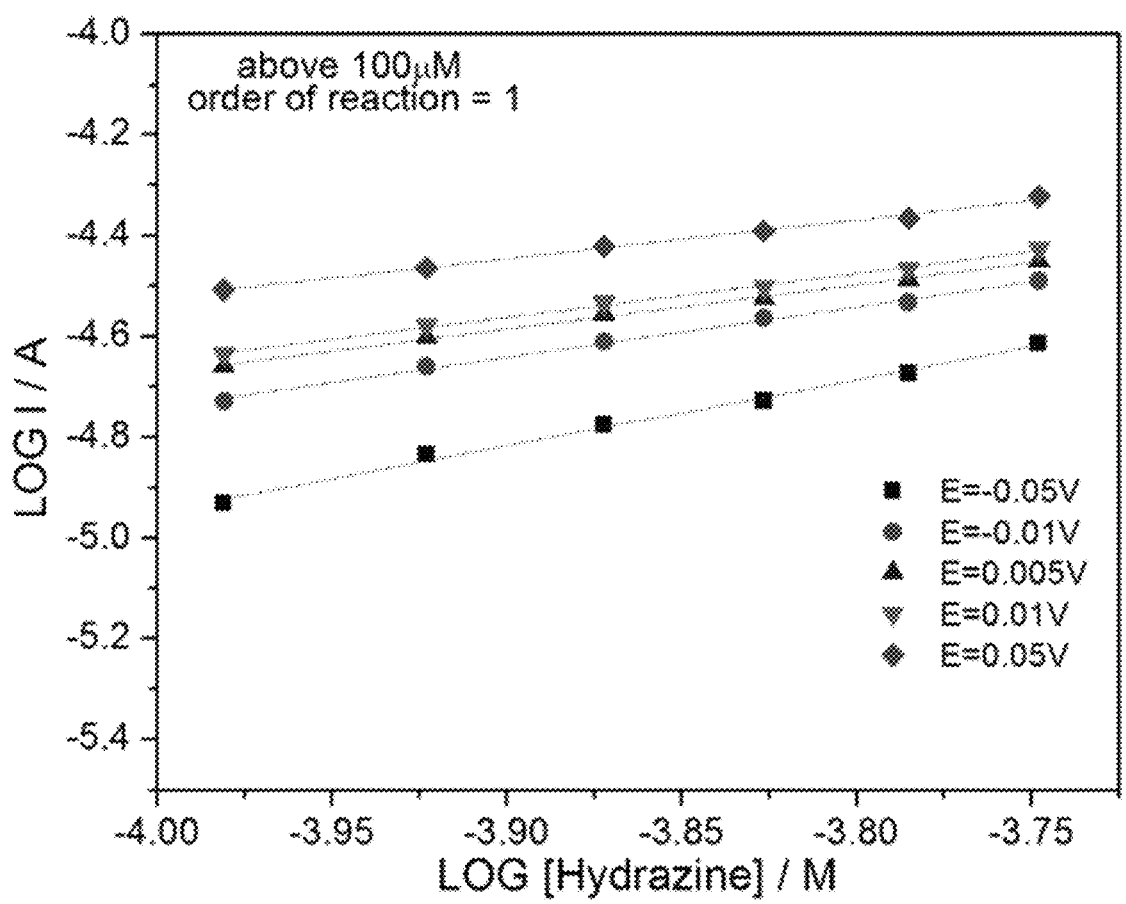
FIG. 8B shows a plot of Log I vs Log [Hydrazine] (above 100 μM) at different potential values (below peak potential), in 0.1 M $K_2SO_4$, with a scan rate of 50 mV/s and a temperature of 25° C.

Log I vs Log [hydrazine] (FIGS. 8A and 8B) at potentials just before the onset of hydrazine oxidation peak potential were plotted to determine the order of reaction. The order of reaction can be deduced from the slope of the straight line from the equation, log I=log k+n log C, where I is the anodic peak current, k is the reaction rate constant, C is the bulk hydrazine concentration, and n is the reaction order. See M. Sohail et al., incorporated herein by reference in its entirety. As deduced from Tafel slopes, below 100 μM, the rate of reaction is directly proportional to the square root of the concentration while above 100 μM, the rate of reaction is directly proportional to concentration.

Figure 9A:
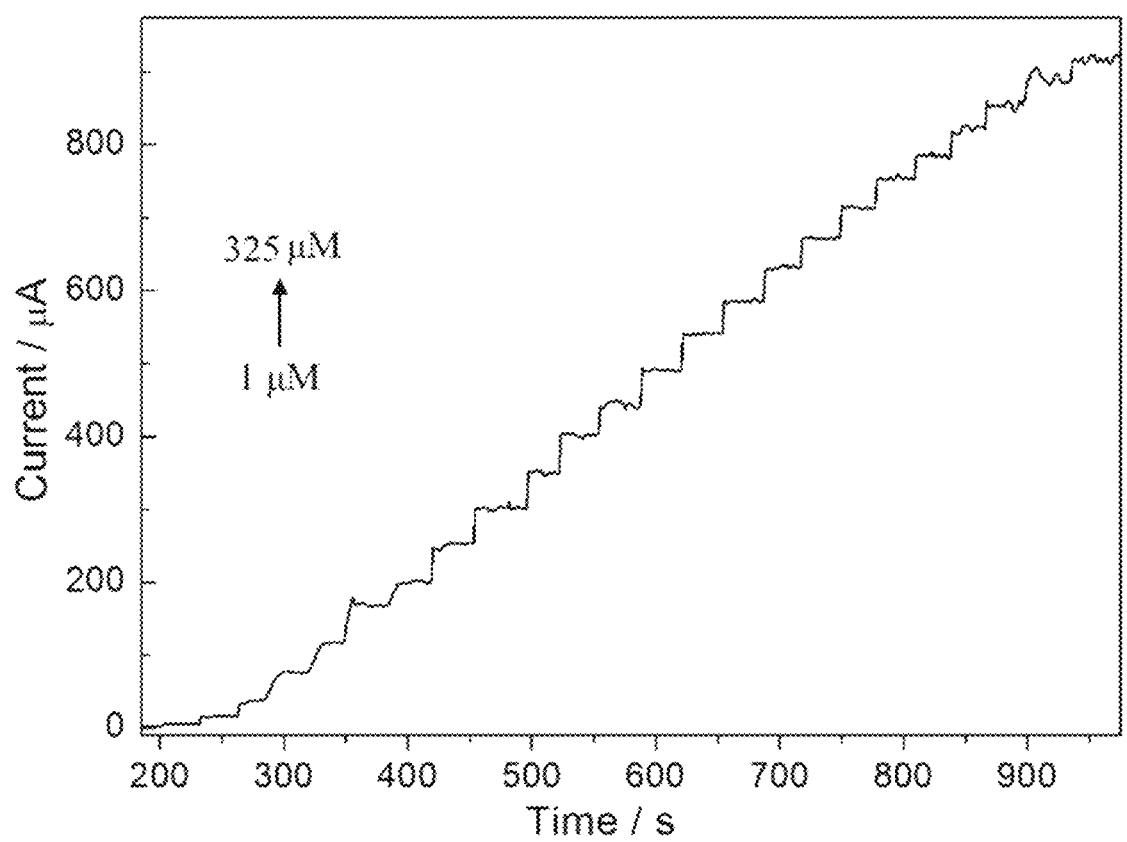
FIG. 9A shows a chronoamperometric response of nanostructured Pd film electrode with successive addition of different concentrations of hydrazine (1-325 μM) in 0.1M $K_2SO_4$ at 0.4 V.
Figure 9B:
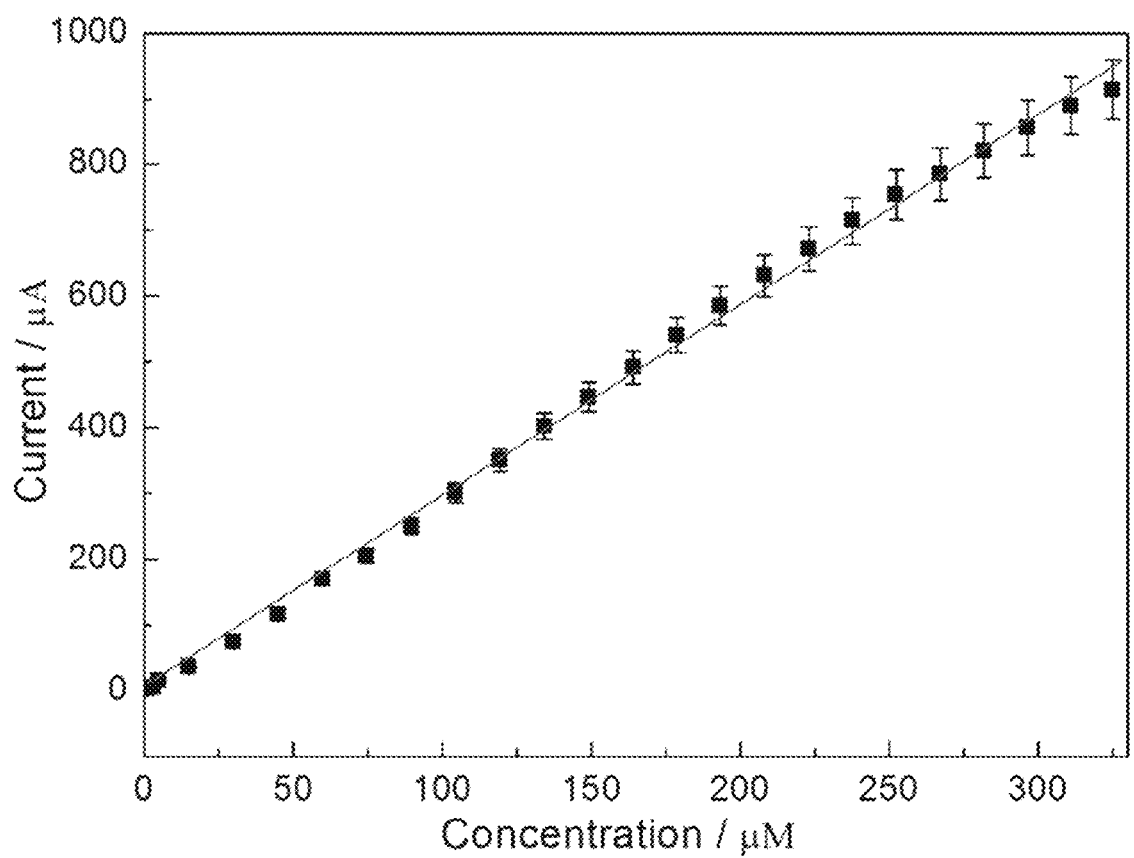
FIG. 9B shows a calibration plot for the hydrazine sensor with the fitted linear equation $I_p(\mu A)$=2.94 [hydrazine] (μM)+9.3×10$^{-4}$.
Figure 18:
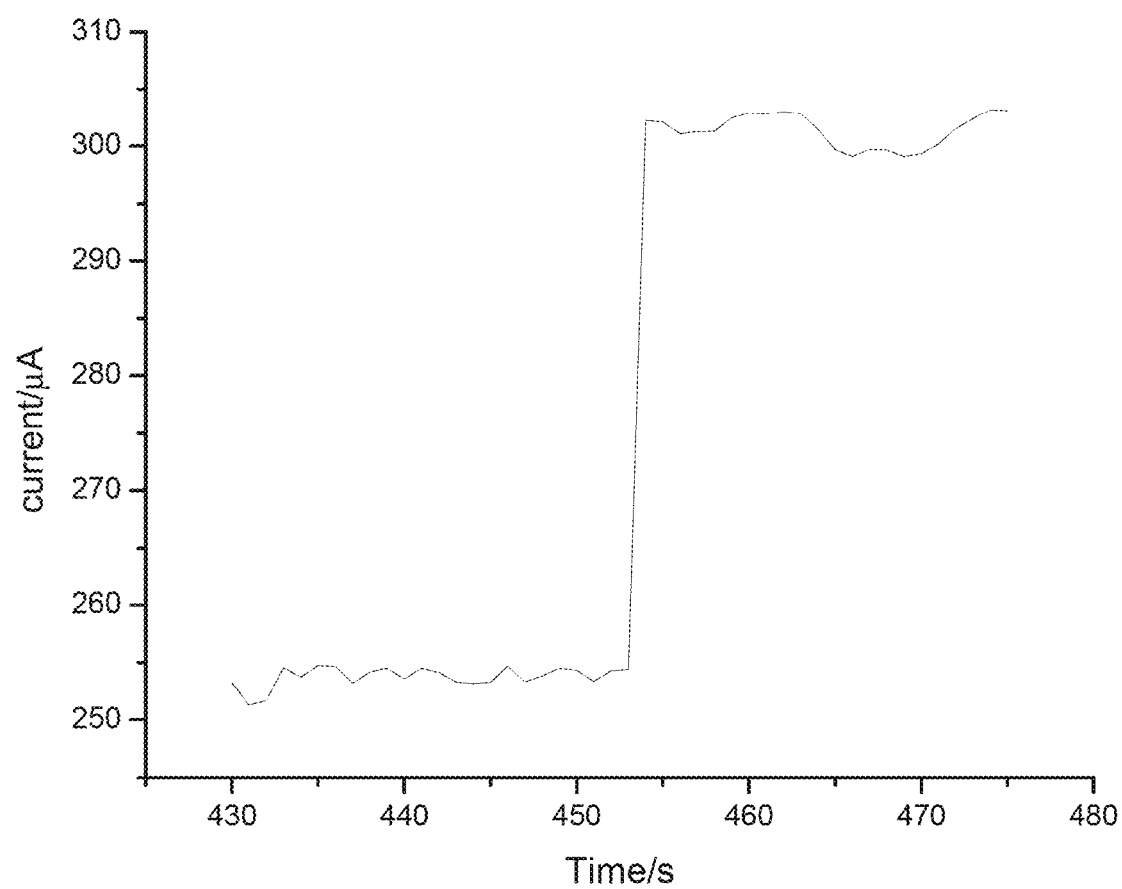
FIG. 18 shows the response time ($T_{res}$) of the sensor to achieve steady-state currents.

FIG. 9A shows the chrono-amperometric response of nanostructured Pd-thin film/FTO electrode with successive additions of hydrazine at regular intervals into 0.1M $K_2SO_4$ at a potential fixed at 0.4 V (vs Ag/AgCl/3M KCl). The data showed that nanostructured Pd-thin film/FTO electrode was sensitive to each addition of hydrazine and gave quick response. The steady state current was achieved within 1 s (FIG. 18), indicating fast electrocatalytic behavior of Pd film electrode. A calibration curve from amperometric response was constructed. From the data (FIG. 9B), a linear relationship was observed between the oxidation peak current (Ip) and hydrazine concentration. The limit of detection (LOD) and limit of quantification (LOQ) were calculated from of the amperometric response of the nanostructured Pd-thin film/FTO electrode for hydrazine concentration as described in literature, and were found to be to be 10 nM and 33 nM, respectively. See P. K. Kannan, C. S. Rout, Chemistry—A European Journal 2015, 21, 9355-9359; and P. K. Kannan, S. A. Moshkalev, C. S. Rout, RSC Advances 2016, 6, 11329-11334, each incorporated herein by reference in their entirety. The sensitivity value was estimated to be 2.94 $\mu A \cdot \mu M^{-1} \cdot cm^{-2}$.

The analytical performance of the nanostructured Pd film electrode was then compared with previously reported materials for hydrazine sensing (Table 1) to get an overview of its sensing performance. It is evident that the nanostructured Pd film produced by AACVD compared well with literature values showing good sensing performance and current sensitivity. In addition to that, the nanostructured Pd-thin film/FTO electrode showed a very low value of LOD and response time (Tres) compared to other reported hydrazine sensors (Table 1). This could be attributed to the higher catalytic ability of nanostructured Pd-thin film for the more effective electrooxidation of hydrazine.

Figure 19:
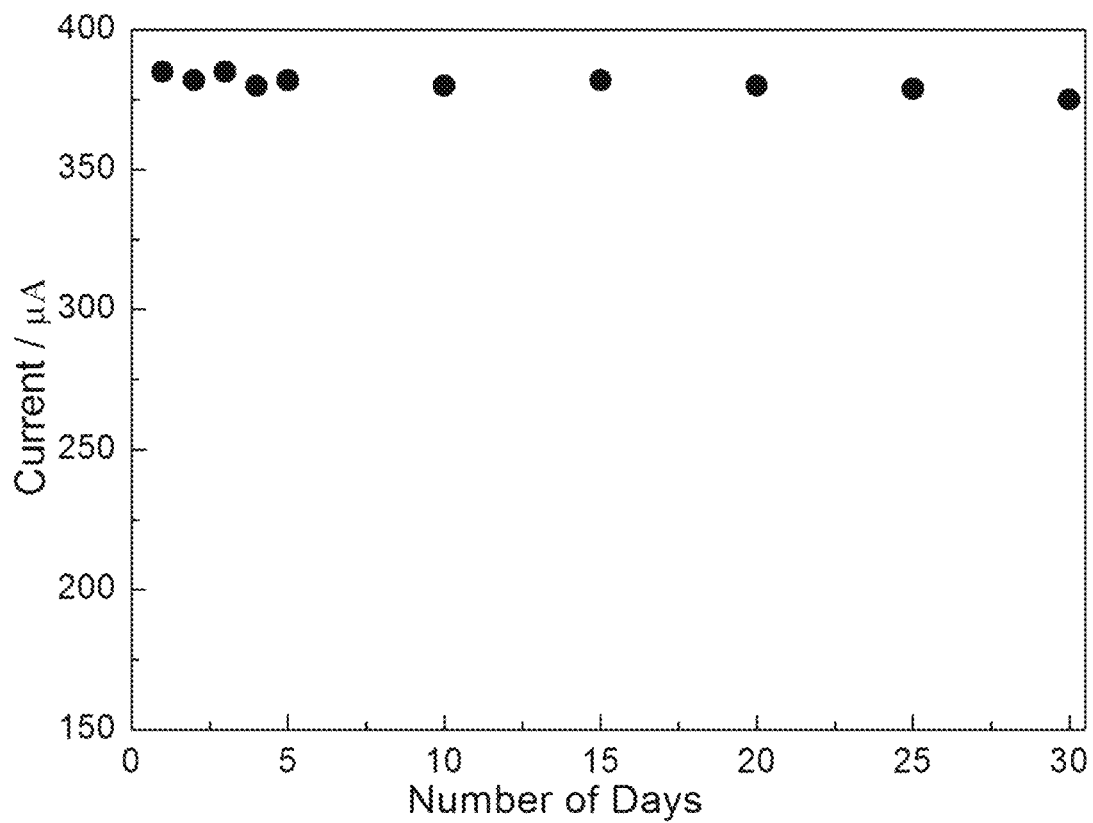
FIG. 19 shows the amperometric response for 120 μM of hydrazine with nanostructured Pd-thin film/FTO electrode after a certain number of days.

The stability and reproducibility of the response for hydrazine oxidation were also studied with the nanostructured Pd-thin film/FTO electrode, and results are shown in FIG. 19. As expected, the Pd-thin film/FTO electrode possessed excellent stability after several days of testing, and no significant loss in current response was noticed over the 30 days of testing period.

TABLE 1

Comparison of detection performance of hydrazine detection using various nanomaterials or nanocomposites by electrochemical approaches.

| Sensor Material | Analytical techniques | Limit of detection (LOD) (μM) | Ref. |
|---|---|---|---|
| PdNPs/rGO | CA | 0.2 | A. Krittayavathananon, et al |
| $TiO_2$ NPs/CGE | LSV | 28.8 | M. M. Rahman, et al. |
| hZnS@Au | CV | 0.667 | F. Feng, et al. |
| Au/SWCNHs/GCE | CV | 1.1 | S. Zhao, et al. |
| Pd/PAMPSA/GCE | CA | 0.42 | V. Lyutov, et al. |
| Nano-Au—ZnO-MWCNT | CV | 0.015 | C. Zhang, et al. |
| Pd/CB/GCE | CA | 8.8 | J. Panchompoo, et al. |
| PdNPs/BDD | LSV | 2.6 | C. Batchelor-McAuley, et al. |
| Pd-thin film/FTO electrode | CA | 0.01 | Present work |

Table references: See A. Krittayavathananon et al.; M. M. Rahman et al.; F. Feng et al.; S. Zhao et al.; V. Lyutov, V. Tsakova, Journal of electroanalytical chemistry 2011, 661, 186-191; C. Zhang, G. Wang, Y. Ji, M. Liu, Y. Feng, Z. Zhang, B. Fang, Sensors and Actuators B: Chemical 2010, 150, 247-253; J. Panchompoo, L. Aldous, C. Downing, A. Crossley, R. G. Compton, Electroanalysis 2011, 23, 1568-1578; and C. Batchelor-McAuley, C. E. Banks, A. O. Simin, T. G. Jones, R. G. Compton Analyst 2006, 131, 106-110, each incorporated herein by reference in their entirety.

In the literature, the electrochemical oxidation of hydrazine is proposed by different chemical reactions as shown in equations (1-3). See B. Dong, B.-L. He, J. Huang, G.-Y. Gao, Z. Yang, H.-L. Li, Journal of Power Sources 2008, 175, 266-271; C. Hu, W. Wang, S. Wang, W. Zhu, Y. Li, Diamond and Related Materials 2003, 12, 1295-1299; T. Pavela, Suomen Kemistilehti B 1975, 30, 240, incorporated herein by reference in its entirety.

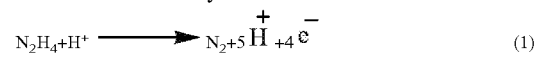

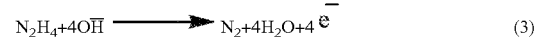

Figure 10:
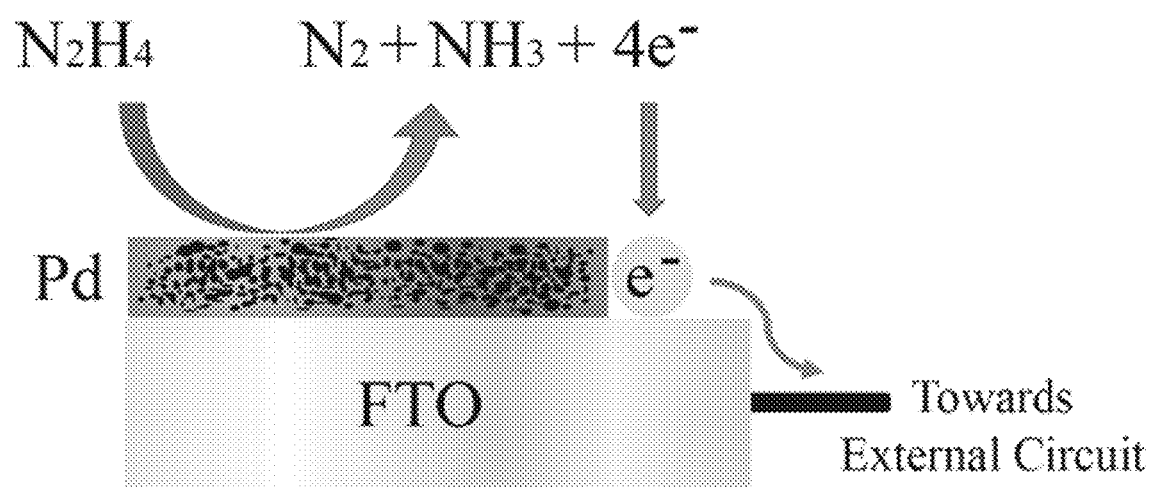
FIG. 10 is a schematic diagram for the nanostructured Pd electrode sensing hydrazine through electrochemical oxidation.

When hydrazine interacts with the nanostructured Pd-thin film/FTO electrode, it releases free electrons on the surface of the electrode, which appear as current signals in an LSV plot. On the basis of above electrochemical results, a plausible mechanism for oxidation of hydrazine is being proposed the scheme shown in FIG. 10.

Aerosol assisted chemical vapor deposition (AACVD) is successfully implemented for the fabrication of nanostructured palladium (Pd) thin films on FTO substrate. The Pd films are produced under the flow of $N_2$ gas and without incorporating hydrogen gas or any other reducing agent while using a palladium acetylacetonate ($Pd(C_5H_7O_2)_2$) precursor. This synthetic strategy can effectively address problems related with conventional CVD approach techniques while depositing palladium thin films with precursors having reduced volatility and thermal stability. The palladium thin films were characterized by powder X-ray diffraction (pXRD), X-ray photoelectron spectroscopy (XPS), scanning electron microscopy (SEM) and energy-dispersive X-ray (EDX) analysis. The newly fabricated palladium nanostructured films were tested for electrochemical sensing of hydrazine. A highly stable and reproducible response for hydrazine oxidation was obtained with a superior limit of detection (LOD) of 10 nM, and limit of quantification (LOQ) of 33 nM, while the sensitivity value calculated was 2.94 $\mu A \cdot \mu M^{-1} \cdot cm^{-2}$. A linear concentration range of 1-325 μM was achieved by chronoamperometry. The synthesized films can be further employed to many other detection systems such as peroxides and peroxide explosives, nitro explosives and electrochemical water oxidation.

The invention claimed is:

1. A method of making a Pd thin film electrode, the method comprising:
   contacting an aerosol with a substrate to deposit a crystalline Pd layer on the substrate and form the Pd thin film electrode,
   wherein the aerosol comprises a carrier gas and a Pd(I) compound dissolved in a solvent, and
   wherein the substrate has a temperature of no greater than 550° C. during the contacting.

2. The method of claim 1, wherein the temperature of the substrate during the contacting is in a range of 400-500° C.

3. The method of claim 1, wherein the aerosol and substrate do not comprise or contact hydrogen gas or a reducing agent during the depositing.

4. The method of claim 1, wherein the Pd thin film electrode comprises
   a Pd film having an average thickness of 0.5-2.0 μm in contact with the substrate, and
   Pd agglomerates on the Pd film.

5. The method of claim 4, wherein the Pd agglomerates have an average diameter of 100-400 nm and comprise Pd nanoparticles having an average diameter of 10-75 nm.

6. The method of claim 1, wherein before the contacting, the aerosol consists essentially of the carrier gas, the solvent, and the Pd(II) compound.

7. The method of claim 1, wherein the palladium(II) compound and the solvent are present in the aerosol at a weight ratio in a range of 1:1000 to 1:2.

8. The method of claim 1, wherein the substrate is a transparent conducting film selected from the group consisting of ITO, FTO, AZO, GZO, IZO, IZTO, IAZO, IGZO, IGTO, and ATO.

9. The method of claim 1, wherein the substrate has a sheet resistance in a range of 1-110 Ω/sq.

10. The method of claim 1, wherein the Pd(II) compound is at least one selected from the group consisting of palladium(II) acetate, palladium(II) bromide, palladium(II) chloride, palladium(II) fluoride, palladium(II) iodide, palladium(II) cyanide, palladium(II) nitrate, sodium tetrachloropalladate, bis(triphenylphosphine)palladium chloride, palladium(II) acetylacetonate, and palladium(II) hexafluoroacetylacetonate.

11. The method of claim 10, wherein the Pd(II) compound is palladium acetylacetonate.

12. The method of claim 1, wherein the solvent is at least one selected from the group consisting of pyridine, N,N-dimethylformamide (DMF), N,N-dimethylacetamide, N-methyl pyrrolidone (NMP), hexamethylphosphoramide (HMPA), dimethyl sulfoxide (DMSO), acetonitrile, tetrahydrofuran (THF), 1,4-dioxane, dichloromethane, chloroform, carbon tetrachloride, dichloroethane, acetone, ethyl acetate, pentane, hexane, decalin, THF, dioxane, benzene, toluene, xylene, o-dichlorobenzene, diethyl ether, methyl t-butyl ether, methanol, ethanol, ethylene glycol, isopropanol, propanol, and n-butanol.

13. The method of claim 12, wherein the solvent is toluene.

14. The method of claim 1, wherein the carrier gas is $N_2$, Ar, or compressed air.

15. The method of claim 1, wherein the aerosol is contacted with the substrate for a time period of 10 min-2 h.

16. The method of claim 1, wherein, during the contacting, the carrier gas has a flow rate in a range of 0.1 to 10 mL/s.

17. The method of claim 1, wherein the Pd thin film electrode is capable of detecting hydrazine in an aqueous solution with a limit of detection (LOD) in a range of 1-50 nM.

18. The method of claim 1, wherein the Pd thin film electrode is capable of detecting hydrazine in an aqueous solution with a limit of quantification (LOQ) in a range of 1-50 nM.

19. The method of claim 1, wherein the Pd thin film electrode is capable of detecting hydrazine in an aqueous solution with a linear chronoamperometric response over a hydrazine concentration of 0.5-350 μM.

* * * * *

UNITED STATES PATENT AND TRADEMARK OFFICE
CERTIFICATE OF CORRECTION

PATENT NO. : 11,437,606 B2
APPLICATION NO. : 16/285653
DATED : September 6, 2022
INVENTOR(S) : Muhammad Ali Ehsan et al.

It is certified that error appears in the above-identified patent and that said Letters Patent is hereby corrected as shown below:

In the Claims

Column 21, Line 7, Claim 1, "a Pd(I)" should read --Pd(II)--.

Signed and Sealed this
Third Day of January, 2023

Katherine Kelly Vidal
*Director of the United States Patent and Trademark Office*